United States Patent
Anderson et al.

(10) Patent No.: US 11,071,587 B2
(45) Date of Patent: *Jul. 27, 2021

(54) METHOD AND APPARATUS FOR TREATING DERMAL MELASMA

(71) Applicant: The General Hospital Corporation, Boston, MA (US)

(72) Inventors: Richard Rox Anderson, Boston, MA (US); Dieter Manstein, Coral Cables, FL (US); Henry Hin Lee Chan, Hong Kong (CN); Vincent Zuo, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/401,988

(22) Filed: May 2, 2019

(65) Prior Publication Data
US 2019/0374287 A1    Dec. 12, 2019

Related U.S. Application Data

(62) Division of application No. 14/911,169, filed as application No. PCT/US2014/050518 on Aug. 11, 2014.
(Continued)

(51) Int. Cl.
*A61B 18/20*    (2006.01)
*A61B 18/00*    (2006.01)

(52) U.S. Cl.
CPC .......... *A61B 18/203* (2013.01); *A61B 18/201* (2013.01); *A61B 2018/00458* (2013.01);
(Continued)

(58) Field of Classification Search
CPC .................................................. A61B 18/203
(Continued)

(56) References Cited

U.S. PATENT DOCUMENTS

| | | |
|---|---|---|
| 5,743,902 A | 4/1998 | Trost |
| 6,287,549 B1 | 9/2001 | Sumian et al. |
| 6,408,212 B1 | 6/2002 | Neev |
| 6,509,548 B1 | 1/2003 | Troitski |
| 6,621,040 B1 | 9/2003 | Perry et al. |
| 6,624,719 B1 | 9/2003 | Anderson et al. |
| 6,695,870 B2 | 2/2004 | Shaw |
| 6,720,521 B2 | 4/2004 | Troitski |
| 6,734,389 B2 | 5/2004 | Troitski |

(Continued)

FOREIGN PATENT DOCUMENTS

| | | |
|---|---|---|
| CN | 1728970 A | 2/2006 |
| JP | 2006-503681 A | 2/2006 |

(Continued)

OTHER PUBLICATIONS

Israeli Office Action dated Jun. 19, 2019 for Israeli Patent Application No. 244030 [cited in parent U.S. Appl. No. 14/911,169, filed Feb. 9, 2016].

(Continued)

*Primary Examiner* — Lynsey C Eiseman
(74) *Attorney, Agent, or Firm* — Hunton Andrews Kurth LLP

(57) ABSTRACT

Exemplary methods and devices can be provided for improving the appearance of dermal melasma. This can be done, e.g., focusing electromagnetic radiation having a wavelength between about 600 nm and 850 nm into a region of the pigmented dermal tissue at a depth between about 150 and 400 microns, using a lens arrangement having a large numerical aperture between about 0.5 and 0.9. The exemplary local dwell time of the focused radiation can be less than a few milliseconds, and a local fluence provided in the focal region can be between about 50 and 500 J/cm². The focal region can be scanned through the dermal tissue at speeds on the order of a few cm/s. Such parameters can provide sufficient energy absorption by pigmented cells in (Continued)

the dermis to disrupt them while avoiding damage to the overlying tissue and unpigmented dermal tissue.

21 Claims, 7 Drawing Sheets

Related U.S. Application Data

(60) Provisional application No. 61/864,238, filed on Aug. 9, 2013.

(52) U.S. Cl.
CPC .............. *A61B 2018/00577* (2013.01); *A61B 2018/20355* (2017.05); *A61B 2018/20361* (2017.05)

(58) Field of Classification Search
USPC .......................................................... 606/9
See application file for complete search history.

(56) References Cited

U.S. PATENT DOCUMENTS

| | | |
|---|---|---|
| 6,787,730 B2 | 9/2004 | Cocci et al. |
| 6,867,387 B2 | 3/2005 | Fugo et al. |
| 6,873,444 B1 | 3/2005 | Guletsky |
| 6,997,923 B2 | 2/2006 | Anderson et al. |
| 7,018,395 B2 | 3/2006 | Chen |
| 7,020,516 B2 | 3/2006 | Flock et al. |
| 7,020,528 B2 | 3/2006 | Neev |
| 7,217,266 B2 | 5/2007 | Anderson et al. |
| 7,244,253 B2 | 7/2007 | Neev |
| 7,270,657 B2 | 9/2007 | Rizoiu et al. |
| 7,326,199 B2 | 2/2008 | MacFarland et al. |
| 7,421,186 B2 | 9/2008 | Boutoussov et al. |
| 7,474,919 B2 | 1/2009 | Ye et al. |
| 7,608,839 B2 | 10/2009 | Coulombe et al. |
| 7,697,814 B2 | 4/2010 | Rizoiu et al. |
| 7,702,196 B2 | 4/2010 | Boutoussov et al. |
| 7,780,652 B2 | 8/2010 | MacFarland et al. |
| 7,824,395 B2 | 11/2010 | Chan et al. |
| 7,887,533 B2 | 2/2011 | Barolet et al. |
| 7,967,016 B2 | 6/2011 | Anderson et al. |
| 7,998,136 B2 | 8/2011 | Jones et al. |
| 8,130,904 B2 | 3/2012 | Bowers et al. |
| 8,246,611 B2 | 8/2012 | Paithankar et al. |
| 8,259,771 B1 | 9/2012 | Shchemelinin et al. |
| 8,264,174 B2 | 9/2012 | Liu et al. |
| 8,523,926 B2 | 9/2013 | Neev |
| 8,672,926 B2 | 3/2014 | Van Hal et al. |
| 8,675,192 B2 | 3/2014 | Ugolin et al. |
| 8,699,026 B2 | 4/2014 | Varghese et al. |
| 8,740,958 B2 | 6/2014 | Anderson et al. |
| 8,932,278 B2 | 1/2015 | Tankovich et al. |
| 8,936,629 B2 | 1/2015 | Boyden |
| 9,161,815 B2 | 10/2015 | Nevo |
| 9,186,066 B2 | 11/2015 | Tearney |
| 9,186,067 B2 | 11/2015 | Tearney |
| 9,202,600 B2 | 12/2015 | Ravn |
| 9,247,995 B2 | 2/2016 | Suckewer |
| 9,254,174 B2 | 2/2016 | Lukac |
| 9,265,576 B2 | 2/2016 | Srinivasan |
| 9,314,302 B2 | 4/2016 | Dougal |
| 9,333,371 B2 | 5/2016 | Bean |
| 9,523,804 B2 | 12/2016 | Wach |
| 9,622,817 B2 | 4/2017 | Van Hal |
| 9,663,754 B2 | 5/2017 | Weltmann et al. |
| 9,695,505 B2 | 7/2017 | O'Donoghue et al. |
| 9,750,572 B2 | 9/2017 | Moeskops et al. |
| 2002/0077678 A1 | 6/2002 | Andersen et al. |
| 2002/0161357 A1 | 10/2002 | Anderson et al. |
| 2002/0169442 A1 | 11/2002 | Neev |
| 2003/0216719 A1 | 11/2003 | Debenedictis et al. |
| 2004/0005349 A1 | 1/2004 | Neev |
| 2004/0158192 A1 | 8/2004 | Kollias et al. |
| 2005/0049582 A1* | 3/2005 | DeBenedictis ........ A61B 18/20 606/9 |
| 2005/0055055 A1 | 3/2005 | Neev |
| 2005/0058701 A1 | 3/2005 | Gross et al. |
| 2005/0065503 A1 | 3/2005 | Anderson et al. |
| 2005/0224460 A1 | 10/2005 | Hutson et al. |
| 2005/0256519 A1 | 11/2005 | Goble et al. |
| 2006/0004306 A1 | 1/2006 | Altshuler et al. |
| 2006/0095097 A1 | 5/2006 | Dees et al. |
| 2007/0045252 A1 | 3/2007 | Kleine et al. |
| 2007/0045255 A1 | 3/2007 | Kleine et al. |
| 2007/0198003 A1 | 8/2007 | Domankevitz et al. |
| 2007/0213695 A1 | 9/2007 | Perl et al. |
| 2007/0260230 A1 | 11/2007 | Youngquist et al. |
| 2007/0299331 A1 | 12/2007 | Friedman et al. |
| 2008/0058783 A1 | 3/2008 | Altshuler et al. |
| 2008/0243110 A1* | 10/2008 | Kang ................... A61B 18/203 606/9 |
| 2008/0262488 A1 | 10/2008 | Penny et al. |
| 2008/0287941 A1 | 11/2008 | Jones et al. |
| 2009/0093799 A1* | 4/2009 | Davenport ........... A61N 5/0616 606/9 |
| 2010/0063490 A1 | 3/2010 | Verhagen et al. |
| 2010/0069897 A1 | 3/2010 | Spikker et al. |
| 2010/0100084 A1 | 4/2010 | Girard et al. |
| 2010/0160903 A1 | 6/2010 | Krespi |
| 2010/0217254 A1 | 8/2010 | Mehta |
| 2010/0249771 A1 | 9/2010 | Mehta et al. |
| 2010/0292684 A1 | 11/2010 | Cynulski et al. |
| 2010/0312054 A1 | 12/2010 | Beyar et al. |
| 2011/0036991 A1 | 2/2011 | Oshemkov et al. |
| 2011/0130618 A1 | 6/2011 | Edoute et al. |
| 2011/0166562 A1 | 7/2011 | Harschack et al. |
| 2011/0313407 A1 | 12/2011 | Rafailov et al. |
| 2012/0010603 A1 | 1/2012 | Milner et al. |
| 2012/0029394 A1 | 2/2012 | Babaev |
| 2012/0226130 A1 | 9/2012 | De Graff et al. |
| 2012/0226268 A1 | 9/2012 | Liu et al. |
| 2012/0265164 A1 | 10/2012 | Reiterer et al. |
| 2012/0314214 A1 | 12/2012 | Alexander et al. |
| 2014/0017635 A1 | 1/2014 | Fischer |
| 2014/0081255 A1 | 3/2014 | Johnson et al. |
| 2014/0243804 A1 | 8/2014 | Lukac et al. |
| 2014/0379052 A1 | 12/2014 | Myeong et al. |
| 2015/0032191 A1 | 1/2015 | Varghese et al. |
| 2015/0080863 A1* | 3/2015 | Welches ................ A61B 18/20 606/3 |
| 2015/0216598 A1 | 8/2015 | Welches et al. |
| 2015/0257828 A1 | 9/2015 | Tankovich et al. |
| 2015/0327777 A1 | 11/2015 | Kostic et al. |
| 2016/0128777 A1 | 5/2016 | Welches |
| 2016/0149370 A1 | 5/2016 | Marincek et al. |
| 2016/0184019 A1 | 6/2016 | Griffin |
| 2016/0220849 A1 | 8/2016 | Knowlton |
| 2016/0250498 A1 | 9/2016 | Bean et al. |
| 2016/0278924 A1 | 9/2016 | Dahotre et al. |
| 2016/0287894 A1 | 10/2016 | Arai et al. |
| 2016/0310055 A1 | 10/2016 | Zand et al. |
| 2016/0318790 A1 | 11/2016 | Hosseini et al. |
| 2017/0035507 A1 | 2/2017 | Huang |
| 2017/0127507 A1 | 5/2017 | Hunt |
| 2017/0189117 A1 | 7/2017 | Mitchell et al. |
| 2017/0209213 A1 | 7/2017 | Binun et al. |

FOREIGN PATENT DOCUMENTS

| | | |
|---|---|---|
| JP | 2008-500846 A | 1/2008 |
| WO | 2005099369 A2 | 10/2005 |

OTHER PUBLICATIONS

Chinese Office Action dated May 10, 2019 for Chinese Patent Application No. 201480049685.7 [cited in parent U.S. Appl. No. 14/911,169, filed Feb. 9, 2016].

Examination as to formal Requirements invitation to Remedy Deficiencies dated Oct. 2018 for European tent Application No.

(56) References Cited

OTHER PUBLICATIONS 18201589.1 [cited in parent U.S. Appl. No. 14/911,169, filed Feb. 9, 2016].
Notice of Reasons for Rejection dated Jun. 26, 2018 for Japanese Patent Application No. 2016-533490 [cited in parent U.S. Appl. No. 14/911,169, filed Feb. 9, 2016].
International Search Report for International Patent Application No. PCT/US2014/050518 dated Nov. 19, 2014 [cited in parent U.S. Appl. No. 14/911,169, filed Feb. 9, 2016].
International Written Opinion for International Patent Application No. PCT/US2014/050518 dated Nov. 19, 2014 [cited in parent U.S. Appl. No. 14/911,169, filed Feb. 9, 2016].
Extended European Search Report dated Mar. 31, 2017 for European National Phase Application No. 14834457.5 [cited in parent U.S. Appl. No. 14/911,169, filed Feb. 9, 2016].
Notification of the English translation of First Office Action dated Sep. 7, 2017 for Chinese Patent No. 201480049685.7 [cited in parent U.S. Appl. No. 14/911,169, filed Feb. 9, 2016].
Habbema, Louis et al., "Efficacy of Minimally Invasive Nonthermal Laser-Induced Optical Breakdown Technology for Skin Rejuvenation," Lasers Med. Sci., vol. 28, pp. 935-940, 2013 [cited in parent U.S. Appl. No. 14/911,169, filed Feb. 9, 2016].
Tanghetti, Emil. A., "The Histology of Skin Treated with a Picosecond Alexandrite Laser and a Fractional Lens Array," Lasers in Sugery and Medicine, vol. 48, pp. 646-652, 2016 [cited in parent U.S. Appl. No. 14/911,169, filed Feb. 9, 2016].
Varghese, Babu et al., "Influence of Absorption Induced Thermal Initiation Pathway on Irradiance Threshold for Laser Induced Breakdown," Biomedical Optics Express, vol. 6, No. 4, pp. 1234-1240, Apr. 1, 2015 [cited in parent U.S. Appl. No. 14/911,169, filed Feb. 9, 2016].
Tinne, Nadine et al., "Interaction Dynamics of Spatially Separated Cavitation Bubbles in Water," Journal of Biomedical Optics, vol. 15, No. 6, pp. 1-10, Nov./Dec. 2010 [cited in parent U.S. Appl. No. 14/911,169, filed Feb. 9, 2016].
Balu, Mihaela et al., "In Vivo Multiphoton-Microscopy of Picosecond-Laser-Induced Optical Breakdown in Human Skin," Lasers in Surgery and Medicine, vol. 49, pp. 555-562, 2017 [cited in parent U.S. Appl. No. 14/911,169, filed Feb. 9, 2016].
Ye, Jing Yong et al., "Enhancement of Laser-Induced Optical Breakdown Using Metal/Dendrimer Nanocomposites," Applied Physics Letters, vol. 80, No. 10, pp. 1713-1715, Mar. 11. 2002 [cited in parent U.S. Appl. No. 14/911,169, filed Feb. 9, 2016].
Jiao, J. et al., "Modeling of Ultrashort Pulsed Laser Ablation in Water and Biological Tissues in Cylindrical . . . " Appl. Phys. B., vol. 103, pp. 195-205, 2011 [cited in parent U.S. Appl. No. 14/911,169, filed Feb. 9, 2016].
Pustovalov, V.K. et al., "Theoretical Investigations of the Processes of Selective Lasers Interaction with Melanin Granules in Pigmented Tissues for Lasers Applications in Medicine," Laser Physics, vol. 16, No. 7, pp. 1011-1028, 2006 [cited in parent U.S. Appl. No. 14/911,169, filed Feb. 9, 2016].
Varghese, Babu et al., "Effects of Polarization and Apodization on Laser Induced Optical Breakdown Threshold," Optics Express, vol. 21, No. 15, pp. 1-7, Jul. 29, 2013 [cited in parent U.S. Appl. No. 14/911,169, filed Feb. 9, 2016].
Vogel, A. et al., "Mechanisms of Femtosecond Laser Nanosurgery of Cells and Tissues," Appl. Phys. B., vol. 81, pp. 1015-1047, 2005 [cited in parent U.S. Appl. No. 14/911,169, filed Feb. 9, 2016].
Gamaly, E.G. et al., "Laser Ablation of Carbon at the Threshold of Plasma Formation," Appl. Phys. A., vol. 69, pp. 5121-5127, 4999 [cited in parent U.S. Appl. No. 14/911,169, filed Feb. 9, 2016].
Schaffer, Chris B. et al., "Dynamics of Femtosecond Laser-Induced Breakdown in Water from Femtoseconds to Microseconds," Optics Express, vol. 10, No. 3, pp. 196-203, Feb. 11, 2002 [cited in parent U.S. Appl. No. 14/911,169, filed Feb. 9, 2016].
Zhou, J. et al., "Numerical Modeling of Transient Progression of Plasma Formation in Biological Tissues Induced by Short Laser Pulses," Appl. Phys. B. vol. 90, pp. 141-148, 2008 [cited in parent U.S. Appl. No. 14/911,169, filed Feb. 9, 2016].

Naock, Joachim et al., "Influence of Pulse Duration on Mechanical Effects After Laser-Induced Breakdown in Water," Journal of Applied Physics, vol. 83, No. 12, pp. 7488-7495, Jun. 15, 1998 [cited in parent U.S. Appl. No. 14/911,169, filed Feb. 9, 2016].
Loesel, F.H. et al., "Non-Thermal Ablation of Neural Tissue with Femtosecond Laser Pulses," Appl. Phys. b., vol. 66, pp. 121-128, 1998 [cited in parent U.S. Appl. No. 14/911,169, filed Feb. 9, 2016].
Lubatschowski, Holger et al., "Interaction with Biological Tissue," Topics, Appl. Phys., vol. 96, pp. 91-105, 2004 [cited in parent U.S. Appl. No. 14/911,169, filed Feb. 9, 2016].
Zou, Dandan et al., "Chiral Streamers," Physics of Plasmas, vol. 22, pp. 1-6, 2015 [cited in parent U.S. Appl. No. 14/911,169, filed Feb. 9, 2016].
Stewart, Nicholas et al., "Lasers and Laser-Like Devices: Part one," Australasian Journal of Dermatology, vol. 54, pp. 173-183, 2013 [cited in parent U.S. Appl. No. 14/911,169, filed Feb. 9, 2016].
Rau, Lih-Rou et al., "Selective Targeting and Restrictive Damage for Nonspecific Cells by Pulsed Laser-Activated Hyaluronan-Gold Nanoparticles," American Chemical Society, vol. 17, pp. 2514-2521, 2016 [cited in parent U.S. Appl. No. 14/911,169, filed Feb. 9, 2016].
Shin, Min-Kyung et al., "Platelet-Rich Plasma Combined with Fractional Laser Therapy for Skin Rejuvenation," Dermatologic Surgery, vol. 38, No. 4, pp. 623-630, Apr. 2012 [cited in parent U.S. Appl. No. 14/911,169, filed Feb. 9, 2016].
Jha, Nayansi et al., "Treatment of Oral Hyperpigmentation of and Gummy Smile using Laser and Role of Plasma as a Novel Treatment Technique in Dentisty: An Introductory Review," Oncotarget, vol. 8, No. 12, pp. 20496-20509, 2017 [cited in parent U.S. Appl. No. 14/911,169, filed Feb. 9, 2016].
Quinto-Su, Pedro A. et al., "Mechanisms of Laser Cellular Microsurgery," Methods in Cell Biology, vol. 82, pp. 113-151, 2007 [cited in parent U.S. Appl. No. 14/911,169, filed Feb. 9, 2016].
Varghese, Babu et al., "Effects of Polarization and Absorption on Laser Induced Optical Breakdown Threshold for Skin Rejuvenation," Proc. of SPIE, vol. 9740, pp. 1-6, 2016 [cited in parent U.S. Appl. No. 14/911,169, filed Feb. 9, 2016].
Balu, Mihaela et al., "In Vivo Muitiphoton-Microscopy of Picosecond-Laser-Induced Optical Breakdown in Human Skin," Lasers in Surgery and Medicine, vol. 49, pp. 555-562, 2017 [cited in parent U.S. Appl. No. 14/911,169, filed Feb. 9, 2016].
Cencic, Boris et al., "Optodynamic Monitoring of Laser Tattoo Removal," Journal of Biomedical Optics, vol. 17, No. 4, pp. 1-6, Apr. 2012 [cited in parent U.S. Appl. No. 14/911,169, filed Feb. 9, 2016].
Fitzpatrick, R., et al., "A Retrospective Analysis of the Safety Profiles of a New Plasmas Skin Regeneration Device Compared to CO2 Lasers," Mosby-Elsevier, vol. 58, pp. 1-37, 2008 [cited in parent U.S. Appl. No. 14/911,169, filed Feb. 9, 2016].
Zhu, Jiang-Ting et al., "The Efficacy of Autologous Platelet-Rich Plasma Combined with Erblum Fractional Laser Therapy for Facial Acne Scars or Acne," Molecular Medicine Reports, vol. 8, pp. 233-237, 2013 [cited in parent U.S. Appl. No. 14/911,169, filed Feb. 9, 2016].
Minai, Limor et al., "Experimental Proof for the Role of Nonlinear Photoionization in Plasmonic Phototherapy," American Chemical Society, vol. 16, pp. 4601-4607, 2016 [cited in parent U.S. Appl. No. 14/911,169, filed Feb. 9, 2016].
Shore, B.W. et al., "Brief intense Laser Fields in Bulk Matter," Laser Physics, vol. 7, No. 1, pp. 119-125, 1997 [cited in parent U.S. Appl. No. 14/911,169, filed Feb. 9, 2017].
Smith, Nicholas I. et al., "Three-Dimensional Subsurface Microprocessing of Collagen by Ultrashort Laser Pulses," Applied Physics Letters, vol. 78, No. 7, pp. 999-1001, Feb. 12, 2001 [cited in parent U.S. Appl. No. 14/911,169, filed Feb. 9, 2016].
Ushenko, O.G. et al., "Wavelet Analysis for Polarization Inhomogeneous Laser Images of Blood Plasma," Proc. of SPIE, vol. 8338, pp. 1-11, 2011 [cited in parent U.S. Appl. No. 14/911,169, filed Feb. 9, 2016].
Vogel, Aldred, "Nonlinear Absorption: Intraocular Microsurgery and Laser Lithotripsy," Phys. Med. Biol., vol. 42, pp. 895-912, 1997 [cited in parent U.S. Appl. No. 14/911,169, filed Feb. 9, 2016].

(56) References Cited

OTHER PUBLICATIONS

Kincade, K., "Laser-Tissue Interaction—Endogenous Chromophores Alter Plasma Formation During Microsurgery," Pennwell Publ Co., vol. 43, pp. 1-4, Dec. 1, 2007 [cited in parent U.S. Appl. No. 14/911,169, filed Feb. 9, 2016].

Habbema, Louis et al., "Minimally Invasive Non-Thermal Laser Technology using Laser-Induced Optical Breakdown for Skin Rejuvenation," J. Biophotonics, vol. 5, No. 2, pp. 194-199, 2012 [cited in parent U.S. Appl. No. 14/911,169, filed Feb. 9, 2016].

Communication pursuant to Article 94(3) EPC dated Aug. 17, 2020 for European application No. 18201589.1.

Examination Report dated Aug. 6, 2020 for Canadian Application No. 2,920,858.

Notice of Grounds for Rejection dated Jan. 25, 2021 issued for Korean Patent Application No. 10-2016-7006196.

\* cited by examiner

METHOD AND APPARATUS FOR TREATING DERMAL MELASMA

CROSS-REFERENCE TO RELATED APPLICATION(S)

The present application is a divisional of U.S. patent application Ser. No. 14/911,169 filed on Feb. 9, 2015, and also relates to and claims priority from International Patent Application No. PCT/US2014/050518 filed Aug. 11, 2014, and from U.S. Provisional Patent Application Ser. No. 61/864,238 filed Aug. 9, 2013, the entire disclosures of which are incorporated herein by reference in their entireties.

FIELD OF THE DISCLOSURE

Exemplary embodiments of the present disclosure relates to treating pigmented tissue, and more particularly to methods and apparatus for treating dermal melasma.

BACKGROUND INFORMATION

Melasma is a skin disorder of unknown etiology that causes a blotchy hyperpigmentation, often in the facial area. This condition is more common in women than in men. Although the specific cause(s) of melasma may not be well-understood, the pigmented appearance of melasma can be aggravated by certain conditions such as pregnancy, sun exposure, certain medications, such as, e.g., oral contraceptives, hormonal levels, genetics, etc.

Exemplary symptoms of melasma include dark, irregularly-shaped patches or macules, which are commonly found on the upper cheek, nose, upper lip, and forehead. These patches often develop gradually over time. Melasma does not appear to cause any other symptoms, nor have other detrimental effects, beyond the cosmetic discoloration.

Unlike many pigmented structures that are typically present in the epidermal region of skin (i.e., at or near the skin surface), dermal (or deep) melasma is often characterized by widespread presence of melanin and melanophages (including, e.g., excessively-pigmented cells) in portions or regions of the underlying dermis. Accordingly, treatment of dermal melasma (e.g., lightening of the appearance of darkened pigmented regions) can be particularly challenging because of the presence of the greater difficulty in accessing and affecting such pigmented cells and structures located deeper within the skin. Accordingly, conventional skin rejuvenation treatments such as facial peels (laser or chemical), dermabrasion, topical agents, and the like, which primarily affect the overlying epidermis, may not be effective in treating dermal melasma.

It has been observed that application of light or optical energy of certain wavelengths can be strongly absorbed by pigmented cells, thereby damaging them. However, an effective treatment of dermal melasma using optical energy introduces several obstacles. For example, pigmented cells in the dermis must be targeted with sufficient optical energy of appropriate wavelength(s) to disrupt or damage them, which may release or destroy some of the pigmentation and reduce the pigmented appearance. However, such energy can be absorbed by pigment (e.g., chromophores) in the overlying skin tissue, such as the epidermis and upper dermis. This near-surface absorption can lead to excessive damage of the outer portion of the skin, and insufficient delivery of energy to the deeper dermis to affect the pigmented cells therein.

Fractional approaches have been developed that involve application of optical energy to small, discrete locations on the skin that are separated by healthy tissue to facilitate healing. However, such fractional approaches may "miss" many of the pigmented cells in the dermis, and effective targeting of such deeper cells may again result in excessive damage to the nearby healthy tissue.

Therefore, it may be desirable to provide method and apparatus that can effectively target pigmented cells in the dermis and reduce the appearance of melasma, without generating excessive damage to healthy skin tissue or producing other undesirable side effects.

SUMMARY OF EXEMPLARY EMBODIMENTS OF THE DISCLOSURE

Exemplary embodiments of methods and apparatus can be provided for a treatment of dermal melasma and other pigmented defects within the dermis, e.g., to lighten the dark pigmented appearance of dermal melasma. The exemplary embodiments of the methods and apparatus can facilitate selective energy absorption by, and thermal damage to, pigmented structures within the dermis by focusing highly-convergent electromagnetic radiation (EMR), e.g., optical energy, having appropriate wavelengths onto the pigmented regions within the dermis. This exemplary procedure can result in heating and/or thermal damage to the pigmented regions, thereby disrupting the pigment and lightening the appearance of the skin, while avoiding unwanted thermal damage to surrounding unpigmented tissue and the overlying tissue.

According to exemplary embodiments of the present disclosure, an apparatus can be provided that can include a radiation emitter arrangement configured to emit EMR, and an optical arrangement configured to direct the EMR onto the skin being treated and focus it to a focal region within the dermis. A plate that is substantially optically transparent to the EMR can be provided on a portion of the apparatus that is configured to contact the surface of the skin being treated. Such plate can stabilize the pliable skin tissue and facilitate better control of the depth of the focal region below the skin surface. A lower surface of the plate can be substantially planar, or it may optionally be slightly convex or concave. The apparatus can further include a housing or handpiece that can contain these components and facilitate manipulation of the apparatus during its use.

The EMR emitter can include, e.g., a waveguide or optical fiber configured to direct EMR from an external source, an EMR source such as one or more diode lasers, a fiber laser, or the like. If the emitter arrangement includes a source of EMR, it can optionally include a cooling arrangement configured to cool the EMR source(s) and prevent overheating of the source(s). A control arrangement can be provided to control the operation of the emitter arrangement including, e.g., turning the EMR source on and off, controlling or varying the power output of the EMR source, etc.

The EMR can have a wavelengths that is preferably greater than about 600 nm, e.g., between about 625 nm and about 850 nm, or between about 650 nm and 750 nm. Smaller wavelengths (e.g., less than about 600 nm) can be scattered significantly within the skin tissue, thereby having insufficient penetration depth to reach portions of the dermal layer with sufficient fluence and focus. Such smaller wavelengths can also have a very high melanin absorbance, which can generate increased EMR absorption by melanin in the overlying epidermal region and unwanted thermal damage to the surface region. Such smaller wavelengths can also have a higher absorbance by hemoglobin, a competing chromophore, which may be present in blood vessels. Significant EMR absorption by hemoglobin can cause unwanted thermal damage to such vessels. Absorbance of EMR by melanin generally decreases with increasing wavelength, so wavelengths longer than about 850 nm may not be sufficiently absorbed by the dermal melanin to cause local heating and disruption of the pigmented structures.

The exemplary apparatus can include an optical arrangement configured to focus the EMR in a highly convergent beam. For example, the optical arrangement can include a focusing or converging lens arrangement having a numerical aperture (NA) of about 0.5 or greater, e.g., between about 0.5 and 0.9. The correspondingly large convergence angle of the EMR can provide a high fluence and intensity in the focal region of the lens (which can be located within the dermis) with a lower fluence in the overlying tissue above the focal region. Such focal geometry can help reduce unwanted heating and thermal damage in the overlying tissue above the pigmented dermal regions. The exemplary optical arrangement can further include a collimating lens arrangement configured to direct EMR from the emitting arrangement onto the focusing lens arrangement.

The exemplary optical arrangement can be configured to focus the EMR to a focal region having a width or spot size that is less than about 200 µm (microns), for example, less than 100 µm, or even less than about 50 µm, e.g., as small as 10 µm. Such spot size can be selected as a balance between being small enough to provide a high fluence or intensity of EMR in the focal region (to effectively irradiate pigmented structures in the dermis), and being large enough to facilitate irradiation of large regions/volumes of the skin tissue in a reasonable treatment time.

The exemplary optical arrangement can also be configured to direct the focal region of the EMR onto a location within the dermal tissue that is at a depth below the skin surface of between about 120 µm and 400 µm, e.g., between about 150 µm and 300 µm. Such exemplary depth range can correspond to typical observed depths of pigmented regions in skin that exhibits dermal melasma. This focal depth can correspond to a distance from a lower surface of the apparatus configured to contact the skin surface and the location of the focal region.

In further exemplary embodiments of the present disclosure, the positions and/or orientations of the EMR emitter arrangement and/or components of the optical arrangement can be controllable or adjustable relative to one another, such that the path of the EMR can be varied. Such variation in the path of the EMR can provide corresponding variations in the depth, width, and/or location of the focal region within the dermis, and can facilitate treatment of larger volumes of the skin tissue when the apparatus is translated with respect to the skin. Such relative movement of these components can also facilitate movement of the focal region within the skin tissue when the apparatus is held stationary relative to the skin, e.g., to treat larger regions of the skin without moving the overall apparatus.

In still further exemplary embodiments of the present disclosure, the exemplary focusing lens arrangement can include a plurality of micro-lenses, e.g., convex lenses, plano-convex lenses, or the like. Each of the micro-lenses can have a large NA (e.g., between about 0.5 and 0.9). The micro-lenses can be provided in an array, e.g., a square or hexagonal array, to produce a plurality of focal regions in the dermal tissue in a similar pattern. A width of the micro-lenses can be small, e.g., between about 1 mm and 3 mm wide. Micro-lenses 300 that are slightly wider or narrower than this can also be provided in certain embodiments. In yet further exemplary embodiments of the present disclosure, the micro-lenses can include cylindrical lenses, for example, convex cylindrical lenses or plano-convex cylindrical lenses. A width of such cylindrical micro-lenses can be small, e.g., between about 1 mm and 3 mm wide. A length of the cylindrical micro-lenses can be between, e.g., about 5 mm and 5 cm.

The exemplary radiation emitter arrangement and/or the exemplary optical arrangement can be configured to direct a single wide beam of EMR over the entire array of such micro-lenses or a portion thereof to simultaneously generate a plurality of focal regions in the dermis. In further exemplary embodiments, radiation emitter arrangement and/or the optical arrangement can be configured to direct a plurality of smaller beams of EMR onto individual ones of the micro-lenses. Such multiple beams can be provided, e.g., by using a plurality of EMR sources (such as laser diodes), a beam splitter, or a plurality of waveguides, or by scanning a single beam over the individual micro-lenses. If cylindrical micro-lenses are provided, one or more beams of EMR can be scanned over such cylindrical lenses, e.g., in a direction parallel to the longitudinal axis of such cylindrical lenses.

In yet another exemplary embodiment of the present disclosure, the exemplary cylindrical or spherical micro-lenses can different NA values, different sizes or radii, and/or different effective focal lengths than one another. Such variations in the geometry and optical properties of the micro-lenses can facilitate irradiation of larger volumes of the dermis.

The plate configured to contact the skin surface can optionally be provided as part of the focusing lens arrangement, e.g., it can be formed as the lower surface of a plano-convex lens or a plurality of such micro-lenses. The plate can optionally be cooled, e.g., by pre-cooling it prior to use or with an active cooling arrangement (e.g. a Peltier device, a conductive cold conduit, or the like). Such cooling can help protect the epidermis and upper portions of the dermis from unwanted thermal damage. An optical gel or the like (e.g. glycerol or a similar substance) can optionally be provided between the plate and the skin surface to reduce an optical index mismatch between the plate and the skin, thereby improving transmission of the EMR into the skin.

In further exemplary embodiments of the present disclosure, the exemplary apparatus can include one or more sensors configured to detect contact of the apparatus with the skin and/or speed of the apparatus over the skin surface during use. Such exemplary sensors can be coupled to a control arrangement of the EMR emitter or source, and adapted to generate signals capable of varying properties of the EMR, e.g., by varying the power emitted by the emitter arrangement based on the translational speed of the apparatus, by turning off the source(s) of EMR when the apparatus is stationary relative to the skin surface or moved away from the skin, etc. Such sensors and control arrangements can improve safety of the apparatus by preventing excessive irradiation and unwanted thermal damage to the skin.

It can be preferable to limit irradiation time (dwell time) of a particular location in the dermis to a short period of time, e.g., about 1-2 milliseconds or less. Such short dwell times can be achieved, e.g., by configuring the radiation emitter arrangement to provide discrete pulses of EMR. The exemplary interval between such pulses of EMR can be, e.g., on the order of about 50 milliseconds or more to provide spatial separation between regions of the dermis irradiated by successive pulses when the apparatus is translated over the skin. Short dwell times can also be achieved by translating the apparatus over the skin during use, e.g., at speeds of about 1 cm/s or greater, such that the focal region does not remain on a particular location in the dermis for longer than a few milliseconds. In further embodiments, optional sensors can also be used to control the EMR emitted by the apparatus to avoid longer local dwell times.

The power output of the exemplary emitter arrangement can be selected to provide a local fluence within each focal region that is between about 10-1000 J/cm² for EMR having a wavelength of about 650 nm, e.g., between about 50-500 J/cm². The estimated fluence within the focal region can be related to the spot size, local dwell time, and total beam power using conventional equations. Larger or smaller local fluence values can also be used when using faster or slower scan speeds and/or with shorter or longer dwell times, respectively. The fluence can be somewhat lower for shorter wavelengths (which is more readily absorbed by melanin) or larger for longer wavelengths, for which EMR absorption by melanin is weaker.

In further embodiments of the disclosure, a method can be provided for treating dermal melasma that includes focusing at least one beam of EMR onto at least one focal region within the dermis, to generate selective absorption by pigmented cells or structures within the dermis while avoiding unwanted heating and damage to unpigmented tissue and overlying tissue. The EMR wavelength used, focal properties (e.g., NA value, focal depth, spot size), scanning speeds and/or pulsed EMR properties, EMR beam power, fluence within the focal region(s), etc., can be provided in accordance with the various embodiments described herein.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Figure 1A:
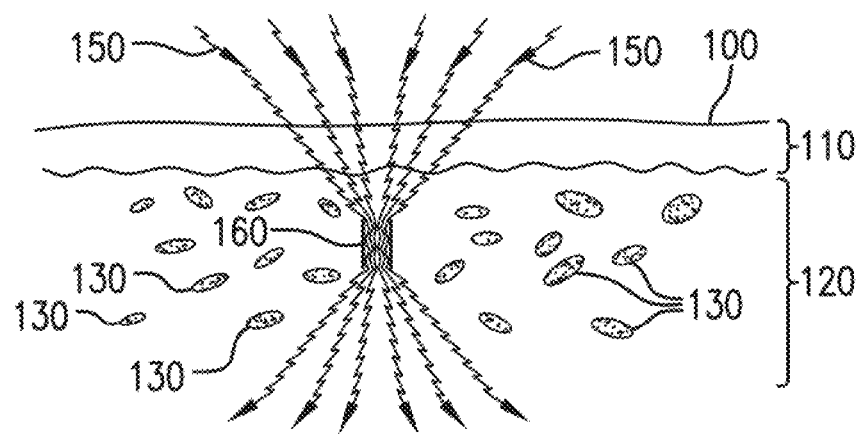
FIG. 1A is a side view of an illustration of one or more radiations being focused into pigmented dermal tissue.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

According to certain exemplary embodiments of the present disclosure, devices and methods can be provided for treating dermal (or deep) melasma. For example, electromagnetic radiation (EMR) such as, e.g., optical energy) at one or more particular wavelengths can be focused into the dermis, where the EMR can optionally be pulsed and/or scanned, such that the radiation is selectively absorbed by the pigmented cells in the dermis. Such absorption of the energy, together with the focusing geometry and scanning parameters, can selectively damage or destroy many of the pigmented cells while reducing or avoiding damage to surrounding unpigmented cells and to the overlying epidermis.

An exemplary schematic side view of a section of skin tissue is shown in FIG. 1. The skin tissue includes a skin surface 100 and an upper epidermal layer 110, or epidermis, which can be, e.g., about 60-120 μm thick in the facial region. The dermis can be slightly thicker in other parts of the body. The underlying dermal layer 120, or dermis, extends from below the epidermis 110 to the deeper subcutaneous fat layer (not shown). Skin exhibiting deep or dermal melasma can include a population of pigmented cells or regions 130 that contain excessive amounts of melanin.

In exemplary embodiments of the present disclosure, an electromagnetic radiation (EMR) 150 (e.g., optical energy) can be focused into one or more focal regions 160 that can be located within the dermis 120. The EMR 150 can be provided at one or more appropriate wavelengths that can be absorbed by melanin. The EMR wavelength(s) can be selected to enhance selective absorption by the pigmented regions 130 in the dermis 120.

Figure 1B:
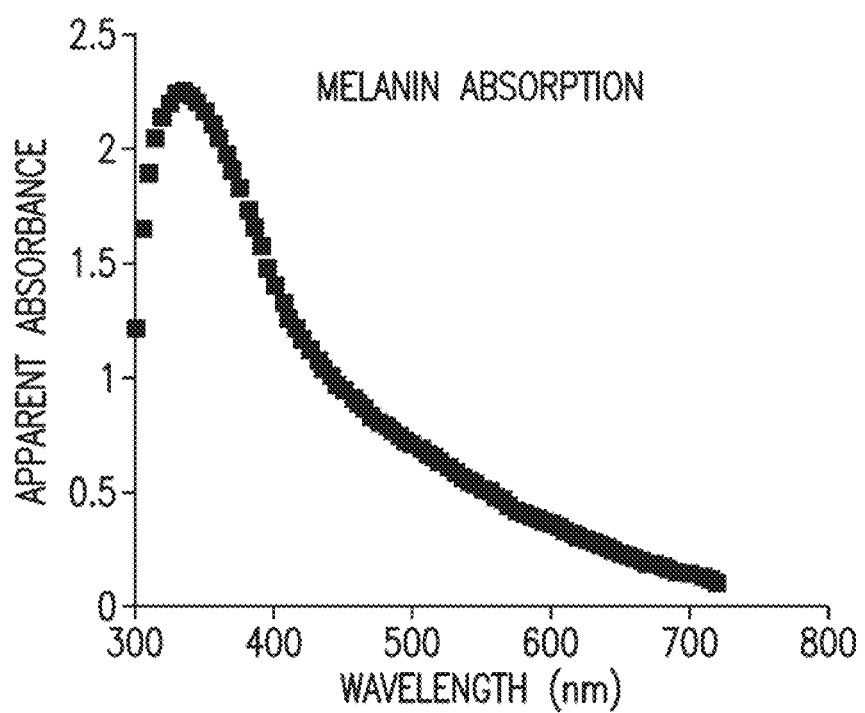
FIG. 1B is an exemplary absorbance spectrum graph for melanin.

For example, a graph of an exemplary absorption spectrum for melanin is shown in the graph of FIG. 1B. The absorption of EMR by melanin is observed to reach a peak value at a wavelength of about 350 nm, and then decreases with increasing wavelength. Although absorption of the EMR by the melanin facilitates heating and/or disruption of the melanin-containing regions 130, a very high melanin absorbance can result in high absorption by pigment in the epidermis 110 and reduced penetration of the EMR into the dermis 120. As illustrated in FIG. 1B, melanin absorption at EMR wavelengths that are less than about 500 nm are relatively high, such that wavelengths less than about 500 nm may not be suitable for penetrating sufficiently into the dermis 120 to heat and damage or disrupt pigmented regions 130 therein. Such enhanced absorption at smaller wavelengths can result in unwanted damage to the epidermis 110 and upper (superficial) portion of the dermis 120, with relatively little unabsorbed EMR passing through the tissue into the deeper portions of the dermis 120.

Figure 1C:
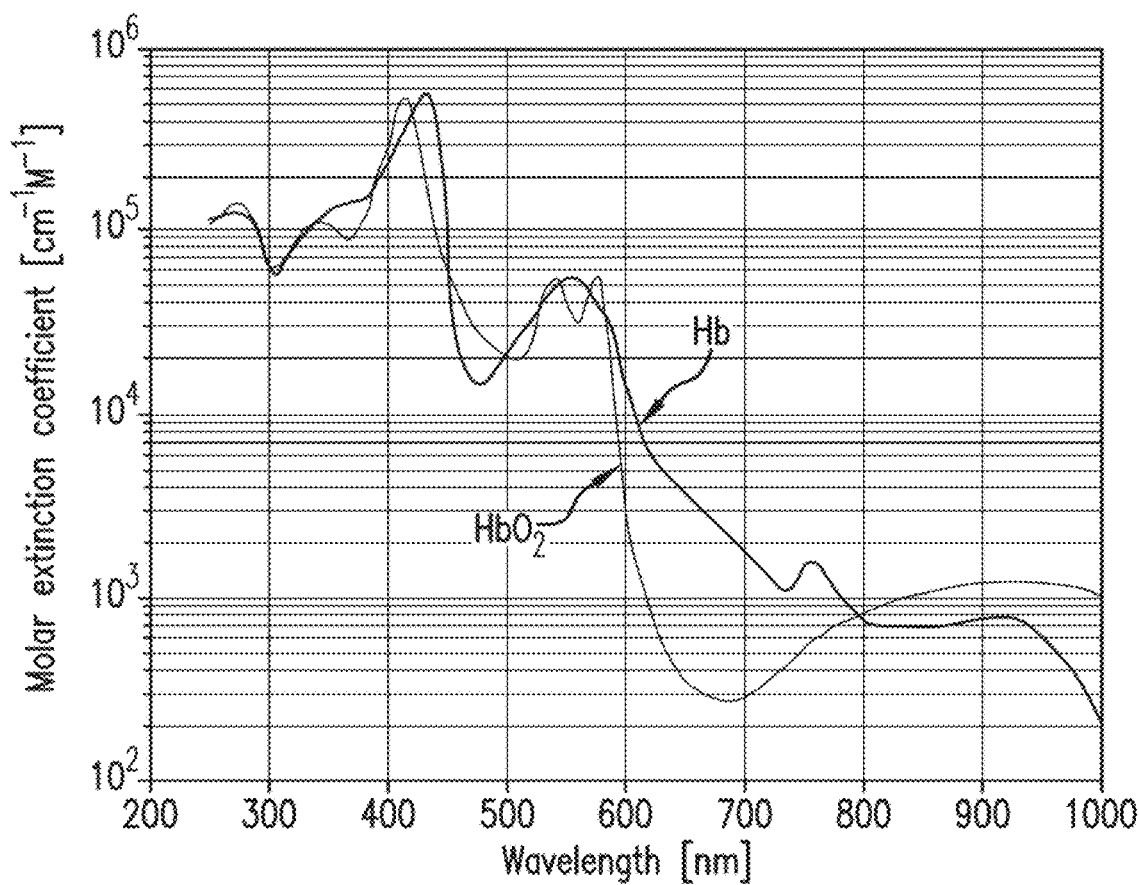
FIG. 1C is an exemplary absorbance spectrum graph for oxygenated and deoxygenated hemoglobin.

Another significant chromophore observed in skin tissue is hemoglobin, which is present in blood vessels. Hemoglobin can be oxygenated ($HbO_2$) or deoxygenated (Hb), where each form of Hemoglobin may exhibit slightly different EMR absorption properties. For example, exemplary absorption spectra for both Hb and $HbO_2$ are shown in the graph of FIG. 1C. These spectra indicate a high absorption coefficient for both Hb and $HbO_2$ at EMR wavelengths less than about 600 nm, with the absorbance decreasing significantly at higher wavelengths. Strong absorption of EMR directed into skin tissue by hemoglobin (Hb and/or $HbO_2$) can result in heating of the hemoglobin-containing blood vessels, resulting in unwanted damage to these vascular structures and less EMR available to be absorbed by the melanin.

Accordingly, it can be preferable to use EMR having wavelengths greater than 600 nm in certain exemplary embodiments of the present disclosure, e.g., about 625 nm or greater. Such wavelengths can increase selectivity of EMR absorption in the dermis, e.g., by reducing competing absorption by hemoglobin, and by also avoiding excessive absorption of the EMR by epidermal melanin (as described above) such that the EMR can penetrate into the dermis 120 and target pigmented regions 130 therein.

For example, longer wavelengths of EMR tend to be scattered more easily by the non-homogeneous structure of skin tissue. Such scattering can reduce the effective penetration depth of EMR directed onto the tissue, and also inhibit focusing of the EMR beam 150 into a small focal region 160 as described herein. Further, the absorbance of melanin continues to decrease with increasing wavelength, as indicated in the graph of FIG. 1B. Thus, EMR having wavelengths less than about 750 nm or 850 nm be well-focused in tissue to generate sufficient local intensity within the dermis 120, as well as sufficiently absorbed by dermal melanin to disrupt and/or damage pigmented regions 130.

Accordingly, exemplary embodiments of the present disclosure, it is possible to provide or use EMR having one or more wavelengths between about 600 nm and about 850 nm, e.g., between about 625 nm and about 800 nm, which is mostly in the visible range of light. In certain embodiments, the wavelength can be between about 650 nm and 750 nm. In further exemplary embodiments of the present disclosure, wavelengths less than about 600 nm or greater than about 850 nm may be used, although EMR having such wavelengths may be provided with sufficient focusing and/or appropriate power and fluence, as described herein, to achieve sufficient quantity and selectivity of absorption by melanin in the dermis.

Figure 2:
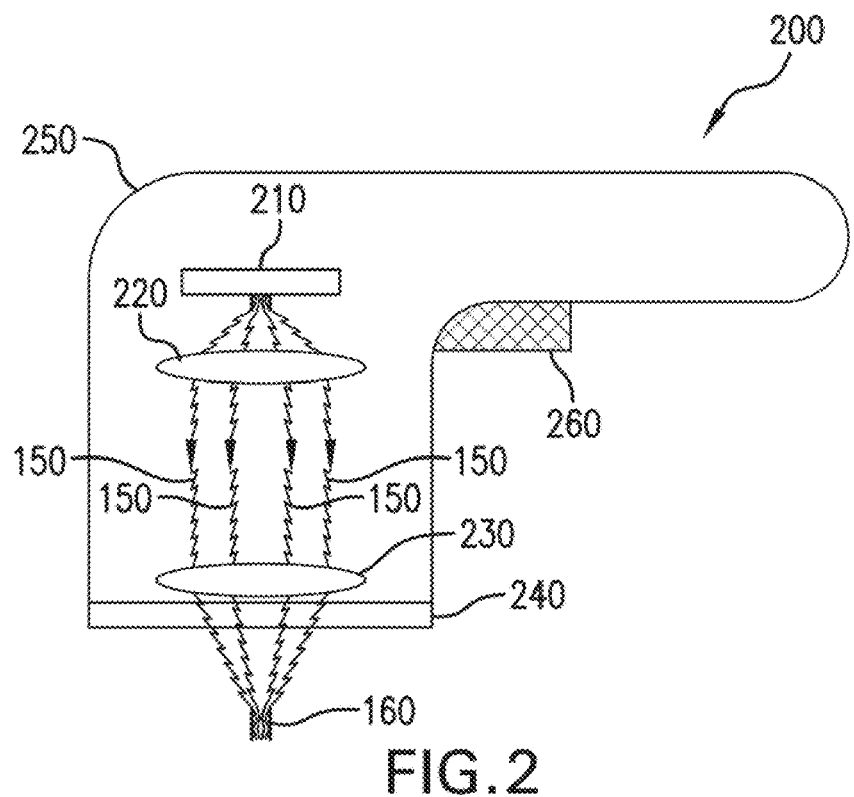
FIG. 2 is a cross-sectional side view of a diagram of an exemplary apparatus in accordance with exemplary embodiments of the present disclosure.

In further exemplary embodiments of the present disclosure, an apparatus 200, schematically illustrated in a diagram of FIG. 2, can be provided to treat dermal melasma in skin using EMR 150, e.g., optical energy. For example, the apparatus 200 can include a radiation emitter arrangement 210, and an optical arrangement that can be provided between the radiation emitter arrangement 210 and the target tissue to be treated. For example, the optical arrangement can include a first lens arrangement 220 and a second lens arrangement 230. These exemplary components can optionally be provided in a handpiece 250 or other housing or enclosure. The apparatus 200 can further include a plate 240 having a lower surface configured to contact the surface 100 of the skin tissue being treated. An actuator arrangement 260 can be provided to control the operation of the apparatus 200, e.g., to activate and/or turn off the emitter arrangement 210, control or adjust certain operational parameters of the apparatus 200, etc. A power source (not shown) for the radiation emitter arrangement 210 can be provided. For example, the power source can include a battery provided within the handpiece 250, an electrical cord or other conductive connection provided between the emitter arrangement 210 and an external power source (e.g. an electrical outlet or the like), etc.

The radiation emitter arrangement 210 can include, e.g., one or more laser diodes, optical fibers, waveguides, or other components configured to generate and/or emit EMR 150 and direct it toward or onto the optical arrangement 220, e.g., onto the first lens arrangement 220. In certain exemplary embodiments of the present disclosure, the radiation emitter arrangement 210 can include one or more laser diodes that emit optical radiation 150 having one or more wavelengths between about 600 nm and 850 nm, e.g., between about 650 nm and 750 nm.

In further exemplary embodiments of the present disclosure, the radiation emitter arrangement 210 can include distal ends of one or more waveguides (e.g., optical fibers) (not shown), where the waveguides can be configured or adapted to direct EMR 150 from an external source (not shown) toward or onto the first lens arrangement 220. Such exemplary external EMR source can be configured to provide or direct EMR 150 to the radiation emitter arrangement 210 having one or more wavelengths between about 600 nm and 850 nm, e.g., between about 650 nm and 750 nm.

In further exemplary embodiments of the present disclosure, the electromagnetic radiation (EMR) 150 (e.g., optical energy) can be focused into one or more focal regions 160 that can be located within the dermis 120, as shown schematically in FIGS. 1A and 2. The exemplary optical arrangement can be configured to provide one or more highly-convergent beams of EMR 150, where each such beam can be emitted from a lower portion of the apparatus 200 and converge to a narrower focal region 160 located at a particular distance below the lower surface of the apparatus 200, e.g., below the lower surface of the plate 240. Such convergence of the EMR 150 can produce a high local fluence and intensity within the focal region 160, while irradiating the overlying tissue (e.g. epidermis 110 and upper portion of the dermis 120) at a lower fluence.

In one additional exemplary embodiment of the present disclosure, the first lens arrangement 220 can be adapted and/or configured to direct EMR 150 from the emitter arrangement 210 towards or onto the second lens arrangement 230. The first lens arrangement 220 can include, e.g., one or more lenses, reflectors, partially- or fully-silvered mirrors, prisms, and/or beam splitters. For example, the first lens arrangement 220 can be configured to collimate or align the EMR 150 emitted from the emitter arrangement 210 onto the second lens arrangement 230, as shown in FIG. 2. The first lens arrangement 220 can include, e.g., an objective lens or the like.

The second lens arrangement 230 can be configured and/or adapted to receive EMR 150 from the first lens arrangement 220, and direct it into one or more focal zones 160 within the dermis 120, as shown in FIG. 1. For example, the first lens arrangement 220 can be a collimating lens, and the second lens arrangement 230 can serve as a focusing lens that includes, e.g., a single objective lens as shown in FIG. 2, one or more plano-convex lenses or cylindrical lenses, or the like. Various exemplary embodiments of the optical arrangement that can be configured to produce one or more focal regions 160 are described in more detail herein below.

For example, as shown in the exemplary illustration in FIG. 2, the highly-convergent beam of EMR 150 is relatively "spread out" as it is passes through the plate 240 (e.g., as it enters the surface 100 of the skin tissue when the apparatus 200 is placed on the skin to irradiate it). Geometrical, temporal, and power characteristics of the EMR 150 can be selected as described herein, such that the fluence and intensity of the EMR 150 at and near the skin surface 100 are sufficiently low to avoid unwanted heating and damage to the surface tissue. The EMR 150 can then be focused to a sufficient intensity and fluence within the focal zone 160 to facilitate significant absorption of the EMR 150 by pigmented regions 130 within or proximal to the focal region 160. In this manner, exemplary embodiments of the present invention can target pigmented regions 130 within the dermis 120 to selectively heat and disrupt or damage them, without generating unwanted damage in the overlying tissue and surrounding unpigmented tissue.

Exemplary beam convergent angles of about 70-80 degrees are illustrated in FIGS. 1A and 2, although this approximate value is merely an exemplary one. In general, the convergent angle can be about 40 degrees or greater, e.g., even about 90 degrees or larger. Such non-narrow convergence angles can generate a large local intensity and fluence of EMR 150 at the focal region 160 while the corresponding fluence in the overlying (and underlying) tissue may be lower due to the beam convergence/divergence. It should be understood that other convergence angles are possible, and are within the scope of the present disclosure.

Accordingly, the effective numerical aperture (NA) of the second lens arrangement 230 is preferably large, e.g., greater than about 0.5, such as between about 0.5 and 0.9. The numerical aperture NA is generally defined in optics as $NA = n \sin \theta$, where n is the refractive index of the medium in which the lens is working, and $\theta$ is one-half of the convergence or divergence angle of the beam. The EMR 150 enters the lens through surrounding air, which has an index of refraction of about 1. Thus, an exemplary convergent half-angle $\theta$ of the beam of EMR towards the focal region 160, corresponding to a NA value between about 0.5 and 0.9, can be between about 30 and 65 degrees. Thus, the exemplary range of the total convergence angle can be between about 60 and 130 degrees.

Larger values of the effective NA can provide a larger convergence angle, and a corresponding greater difference in the local beam intensity and fluence between the tissue surface 100 and the focal region 160. Accordingly, a larger NA value can provide a greater "safety margin" by providing less intense irradiation levels to the overlying tissue than to the pigmented regions 130, thereby reducing the likelihood of generating thermal damage in the overlying tissue. However, a larger NA value can decrease the size of the focal region 160 relative to the area of the incoming EMR beam, which can thereby irradiate a relatively smaller treatment volume of pigmented tissue within the dermis 120. Such smaller treatment volumes can reduce the efficiency of treating large areas of skin in a reasonable time. Exemplary NA values between about 0.5 and 0.9 can thus provide a reasonable compromise between safety factor and treatment efficiency, although slightly larger or smaller values of the NA may be used in certain embodiments (e.g., by adjusting other system parameters appropriately, such as beam power, scanning speed, etc.).

A width of the focal region 160 (e.g., a "spot size") can be small, e.g., less than about 200 μm, for example, less than 100 μm. In general, the focal region can be defined as the volumetric region in which the EMR 150 is present at a highest intensity. For example, the focal region 160 may not be present as an idealized spot because of such factors as scattering of the EMR 150 within the tissue, aberrations or nonidealities in the optical components (e.g. lenses and/or reflectors), variations in the path of the incident rays of EMR 150, etc. Further, the focal region 160 can be spread over a small range of depths within the tissue, as shown schematically in FIGS. 1A and 2. In general, the size and location of the focal region relative to the apparatus 200 can be determined or selected based on properties and configuration of the optical arrangement (e.g., the first and second lens arrangements 220, 230), the characteristics of the EMR 150 provided by the emitting arrangement 210, and optical properties of the skin tissue being treated.

In certain exemplary embodiments, the width of the focal region 160 can be less than 50 μm, e.g., as small as 10 μm. For example, a theoretical lower for the spot size can be approximated as $1.22\lambda/NA$, where $\lambda$ is the wavelength of the electromagnetic radiation and NA is the numerical aperture of a lens. For a wavelength of about 650 nm and a NA of 0.5, the theoretical minimum spot size is about 1.6 microns. The actual spot size (or width of the focal region 160) can be selected as a balance between being small enough to provide a high fluence or intensity of EMR 150 in the focal zone 160 (to damage pigmented cells 130), and being large enough to irradiate a sufficiently large volume of the skin tissue in a short time. Also, a larger focal spot size can reduce the difference in fluence between the focal region and the overlying tissue for a given NA value, thereby increasing the possibility of unwanted heating and/or damage to overlying tissue.

For a particular exemplary NA value of the focusing lens arrangement 230, the beam radius at the surface can be estimated as the focal depth multiplied by the tangent of the half-angle of convergence provided by the focusing lens. As an example, an NA value of 0.5 corresponds to a convergence half-angle of about 30 degrees, for which the tangent is 0.577. For an exemplary focal depth of 200 microns, the radius of the converging EMR beam at the skin surface 100 is about 115 microns (0.577×200), such that the total beam width at the surface is about 230 microns. The local fluence is inversely proportional to the local cross-sectional area of the beam for a particular beam energy. Accordingly, for a spot size (focal region width) of 20 microns, the ratio of fluence at the focal region to that at the skin surface is about $(230/20)^2$, or about 130:1. The actual fluence ratio may be somewhat less due to absorption of some of the EMR energy between the skin surface and the focal region. Nevertheless, this exemplary calculation indicates the relatively low fluence in the surface regions of the skin (as compared to the fluence in the focal region) that can be generated when using a focusing lens having a high NA.

In further exemplary embodiments of the present disclosure, a plurality of such focal regions 160 can be generated simultaneously by the exemplary apparatus and/or the focal region(s) 160 may be scanned or traversed through the portions of dermis 120 containing pigmented cells 130 to irradiate larger volumes of the dermis 120 in a reasonable time, as described in more detail herein.

In certain exemplary embodiments, the depth of the focal region 160 below the skin surface 100 can be between about 120 µm and 400 µm, e.g., between about 150 µm and 300 µm. This exemplary depth range can generally correspond to the observed depths of pigmented regions 130 in skin that exhibits dermal melasma. The focal depth can correspond to a distance from a lower contact surface of the apparatus 200 (e.g., the lower surface of the plate 240) and the focal region 160 of the EMR 150, because the plate 240 may flatten out the underlying tissue when placed on the skin surface 100. Accordingly, the depth of the focal region 160 within the skin may be selected or controlled based on a configuration of the optical arrangement within the housing 250.

In various exemplary embodiments of the present disclosure, the EMR 150 can be collimated (e.g., rays within the EMR beam are substantially parallel to one another), convergent, or divergent between the first lens arrangement 220 and second lens arrangement 230. In still further exemplary embodiments, the radiation emitter arrangement 210 and/or components of the optical arrangement (e.g., the first lens arrangement 220 and/or the second lens arrangement 230) can be controllable or adjustable such that the path of the EMR 150 can be varied. Such exemplary variation in the path of the EMR 150 can provide corresponding variations in the depth, width, and/or location of the focal region 160 within the dermis 120 when the apparatus is held stationary with respect to the skin.

For example, the position and/or angle of the EMR 150 can be shifted relative to the optical axis of a lens in the second lens arrangement 230. Alternatively or additionally, the convergence or divergence of the EMR 150 entering or within the optical arrangement can be varied. Such variations in the EMR geometry and/or path can provide variations in the depth and/or lateral position of the focal region(s) 160. In this manner, larger volumes of the dermis 120 can be irradiated while the apparatus 200 is held stationary over the area of skin being treated. Such exemplary variation of the focus region characteristics can facilitate treatment of a plurality of depth ranges and/or locations within the dermis 120 containing pigmented cells or defects 130.

Exemplary adjustment and/or alteration of the geometry and/or path of the EMR 150 can be achieved, e.g., using one or more translators, movable mirrors, beam splitters and/or prisms, or the like, which may be coupled to the radiation emitter arrangement 210, the first lens arrangement 220, and/or the second lens arrangement 230. Further, these exemplary variations in locations of the focal region 160 can also be combined with a translation of the apparatus 200 over the area of skin being treated to irradiate larger volumes of the dermis 120, thereby targeting a greater number of pigmented cells 130 that can be present.

Figure 3A:
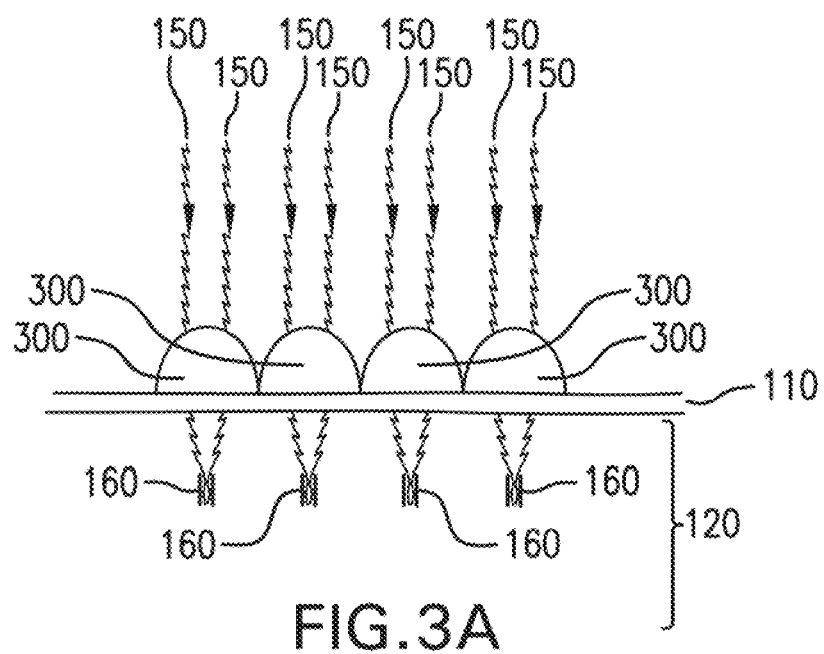
FIG. 3A is a schematic side view of an arrangement of micro-lenses that can be used with certain exemplary embodiments of the present disclosure.

In further exemplary embodiments of the present disclosure, the second lens arrangement 230 can include a plurality of micro-lenses 300, e.g., as provided in a schematic side view of the exemplary configuration illustrated in FIG. 3A. For example, the micro-lenses 300 can include any conventional type of convergent lenses, e.g., convex lenses, or plano-convex lenses such as those shown in FIG. 3A. The micro-lenses 300 can be configured to focus EMR 150 into a plurality of focal regions 160 within the underlying dermis 120, as illustrated in FIG. 3A.

Each of the micro-lenses can have a large NA (e.g., between about 0.5 and 0.9), such that the EMR 150 converges from a relatively wide area at or near the skin surface 100 (with a relatively low intensity or local fluence) to a small width (with higher intensity or local fluence) in the focal region 160 within the dermis 120. Such optical properties can provide a sufficient intensity of EMR 150 within the focal region 160 to damage pigmented cells that absorb the radiation 150, while avoiding areas or volumes of high fluence or intensity away from the volume of dermis 120 containing pigmented cells 130, thereby reducing likelihood of damaging overlying, underlying, and/or adjacent volumes of unpigmented skin tissue.

Figure 3B:
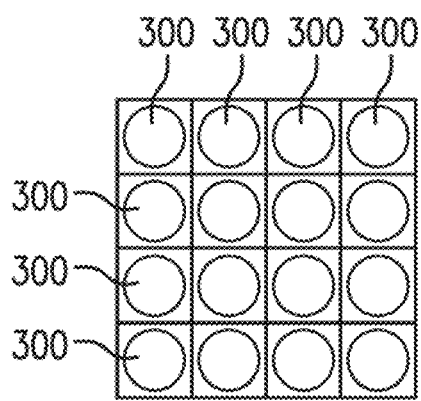
FIG. 3B is a schematic top view of a first exemplary arrangement of the micro-lenses shown in FIG. 3A.
Figure 3C:
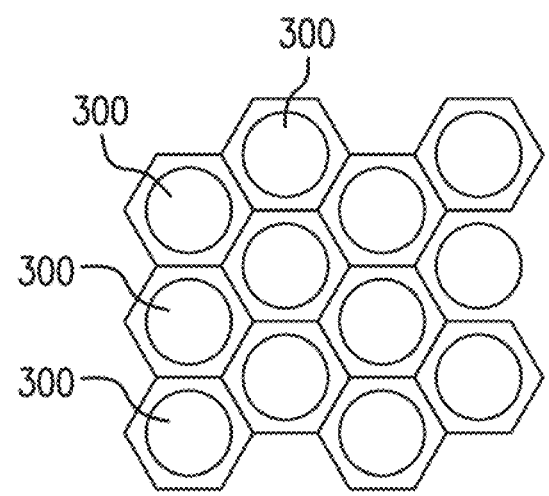
FIG. 3C is a schematic top view of a second exemplary arrangement of the micro-lenses shown in FIG. 3A.

The micro-lenses 300 can be provided in a substantially square or rectangular array, such as that shown in the top view of such exemplary configuration in FIG. 3B. According to further exemplary embodiments of the present disclosure, the micro-lenses 300 can be provided in a hexagonal array, as shown in FIG. 3C. Other exemplary patterns and/or shapes of the micro-lenses 300 can be provided in still further exemplary embodiments. A width of the micro-lenses 300 can be small, e.g., between about 1 mm and 3 mm wide. The exemplary micro-lenses 300 that are slightly wider or narrower than this can also be provided in certain exemplary embodiments.

In additional exemplary embodiments of the present disclosure, the radiation emitter arrangement 210 and/or the first lens arrangement 220 can be configured to direct a single wide beam of EMR 150 (such as, e.g., that shown in FIG. 2) over the entire array of micro-lenses 300 or a substantial portion thereof. Such exemplary configuration can generate a plurality of focal regions 160 in the dermis 120 simultaneously. In further exemplary embodiments, the radiation emitter arrangement 210 and/or the first lens arrangement 220 can be configured to direct a plurality of smaller beams of EMR 150 onto individual ones of the micro-lenses 300. According to still further exemplary embodiments, the radiation emitter arrangement 210 and/or the first lens arrangement 220 can be configured to direct one or more smaller beams of EMR 150 onto a portion of the array of micro-lenses 300, e.g. onto a single micro-lens or a plurality of the micro-lenses 300, and the smaller beam(s) can be scanned over the array of the micro-lenses 300, such that a plurality of the focal regions 160 can be generated sequentially or non-simultaneously in the dermis 120.

Figure 3D:
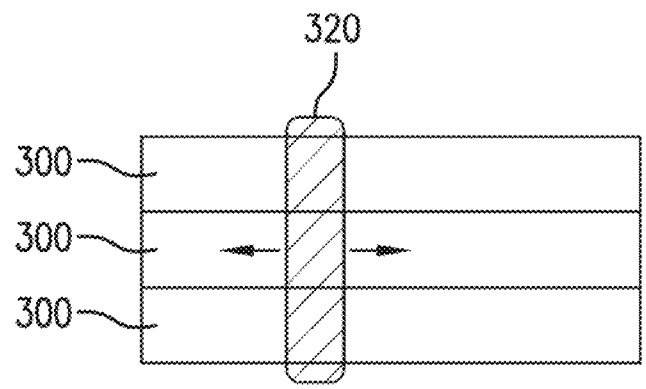
FIG. 3D is a schematic top view of an exemplary arrangement of cylindrical micro-lenses that can be used with certain exemplary embodiments of the present disclosure.
Figure 3E:
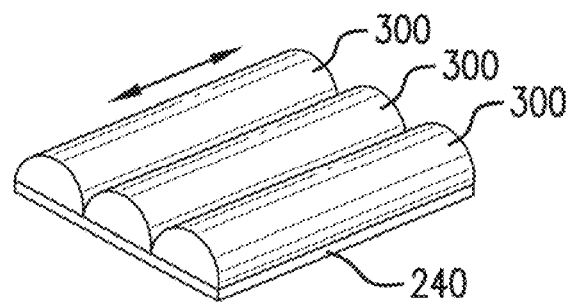
FIG. 3E is a schematic angled view of the exemplary arrangement of cylindrical micro-lenses shown in FIG. 3D.

In yet further exemplary embodiments of the present disclosure, the micro-lenses 300 can include cylindrical lenses, for example, convex cylindrical lenses or plano-convex cylindrical lenses, e.g., as shown in an exemplary top view in FIG. 3D and exemplary angled view in FIG. 3E. In the context used herein, 'cylindrical' does not necessarily require the rounded surface of the lens to be circular; it may have an elliptical or other smooth but non-circular profile in certain embodiments. Such cylindrical lenses can have a uniform profile in any cross-section that is perpendicular to the longitudinal axis of the lens.

A width of the cylindrical micro-lenses 300 can be small, e.g., between about 1 mm and 3 mm wide. The length of the cylindrical micro-lenses 300 can be between about 5 mm and 5 cm, e.g., between about 5 mm and about 2 cm. This width and length can be selected based on such factors as the total power emitted by the radiation emitter arrangement 210, the overall size of the array of micro-lenses 300, etc. In certain exemplary embodiments, cylindrical micro-lenses 300 that are slightly shorter or longer and/or slightly narrower or wider can be provided.

In certain exemplary embodiments of the present disclosure, any of the exemplary arrays of the micro-lenses 300 can be provided on (or formed as part of) the plate 240, as illustrated in FIG. 3E. Such configuration can facilitate placement of the micro-lenses 300 close to the skin surface 100, and also facilitate a more precise depth of the focal regions 160 within the dermis 120, e.g., when the plate 240 contacts the skin surface 100 during use.

In further exemplary embodiments of the present disclosure, the radiation emitter arrangement 210 and/or the first lens arrangement 220 can be configured to direct a single wide beam of EMR 150 (such as that shown in FIG. 2) over the entire array of cylindrical micro-lenses 300 or a substantial portion thereof. Such exemplary configuration can generate and/or produce a plurality of the focal regions 160 in the dermis 120 simultaneously that are elongated in one direction (e.g. along the longitudinal axis of the cylindrical micro-lenses 300) and narrow (e.g., less than about 200 µm wide, less than about 100 µm wide, less than about 50 µm wide, or as small as about 10 µm wide) in a direction orthogonal to the longitudinal axis of the cylindrical micro-lenses 300. Such "line-focused" EMR 150 can be used to more efficiently irradiate larger volumes of the dermis 120, e.g., when the exemplary apparatus 200 is scanned over the area of skin being treated, for example, in a direction substantially orthogonal to (or optionally at some other angle to) the longitudinal axis of the cylindrical micro-lenses 300.

According to yet additional exemplary embodiments of the present disclosure, the radiation emitter arrangement 210 and/or the first lens arrangement 220 can be configured to direct one or more smaller beams of EMR 150 onto one or more of the cylindrical micro-lenses 300. For example, the EMR 150 can be directed onto one or more cylindrical micro-lenses 300, e.g., over an elongated area 320 such as that shown in FIG. 3D. The radiation emitter arrangement 210 and/or the first lens arrangement 220 can be further configured to scan or traverse the irradiated area 320 over the cylindrical micro-lenses 300 (for example, using one or more movable mirrors, prisms, waveguides, or the like in the optical arrangement), e.g., along the longitudinal directions indicated by the arrows shown in FIGS. 3D and 3E (or back and forth along such direction), such that a plurality of the elongated focal regions 160 are progressively generated in the dermis 120 during the scan. Such scanning of the EMR 150 can produce an irradiated focal region 160 having a shape of an extended line within the dermis 120. The apparatus 200 can also be traversed laterally over the region of skin being treated, e.g., in a direction not parallel to the longitudinal axes of the cylindrical micro-lenses 300, during the irradiation such that the elongated focal regions 160 can travel through the dermis 120 and irradiate a larger volume of tissue. For example, as described herein such lateral traversal can be between about 5 mm/sec and 5 cm/sec. The scanning speed of the EMR beam along the axes of the cylindrical can be larger, e.g., greater than about 10 cm/sec, to provide a more uniform irradiation of such larger volumes of tissue. The scan rate of the EMR 150 along the cylindrical lens axes, traversal speed of the apparatus 200 over the skin, power of the EMR emitter arrangement 210, and width of the focal region 160 can be selected to provide a local fluence generated within portions of the the dermis 120 by the elongated focal region 160 that is within the exemplary fluence ranges described herein.

Figure 3F:
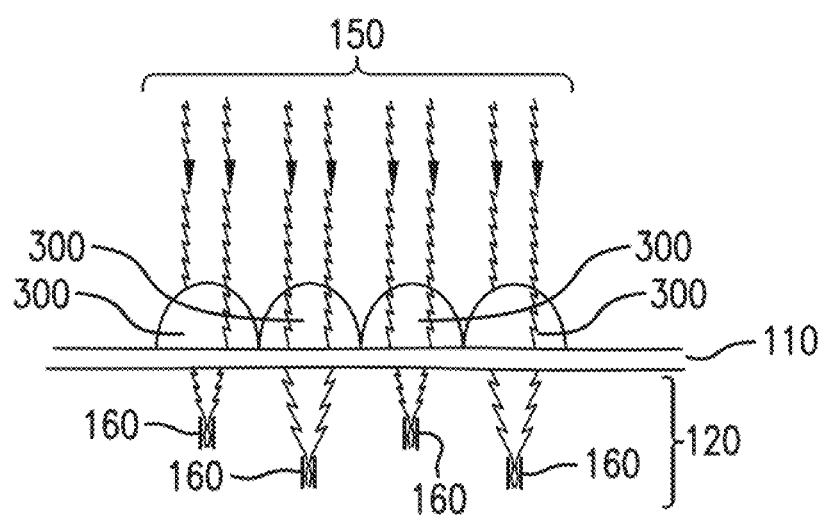
FIG. 3F is a schematic side view of a further exemplary arrangement of the micro-lenses that can be used with further exemplary embodiments of the present disclosure.

In yet further exemplary embodiment of the present disclosure, some of the cylindrical or spherical micro-lenses 300 can have different NA values, different sizes or radii, and/or different effective focal lengths, e.g., as shown in the exemplary schematic diagram in FIG. 3F. The different focal depths of the micro-lenses 300 below the skin surface 100 can be, e.g., between about 120 µm and 400 µm, for example, between about 150 µm and 300 µm. Such exemplary variations in the focal lengths can produce focal regions 160 at different depths, which can result in irradiation of larger volumes of the dermis 120 when the exemplary apparatus 200 is translated over the area of skin being treated, thereby targeting a greater number of pigmented cells 130 that may be present (e.g., irradiating both shallower and deeper pigmented cells 130 in the dermis 120).

The window or plate 240, if present, can be configured and/or structured to contact the surface 100 of the area of skin being treated. The lower surface of the window 240 can be substantially planar, or it may be convex or concave in further embodiments. The window 240 can provide certain benefits during operation of the apparatus 200. For example, the window 240 can facilitate precise positioning of the first and second optical arrangements 220, 230 relative to the skin surface 100, which can facilitate accurate control, selection and/or variation of the depth(s) of the focal region(s) 160 within the skin.

The window 240 can further stabilize the soft skin tissue while it is being irradiated by the apparatus 200, which can facilitate control and uniformity of the irradiation profile. Pressure provided by the window 240 on the skin surface 100 can also blanche (or remove some blood from) the volume of skin tissue being irradiated, thereby reducing the amount of pigmented structures present locally (e.g. blood-filled vessels containing hemoglobin). Such blanching can facilitate increased selectivity of absorption of the EMR 150 by pigmented cells 130 while reducing a risk of unwanted damage to blood vessels.

In exemplary embodiments of the disclosure, the window 240 can be cooled, e.g., by pre-cooling it prior to using the apparatus 200 or by active cooling using a conventional cooling arrangement C (e.g. a Peltier device, a conductive cold conduit, or the like). Such cooling can facilitate protection of the epidermis 110 and/or upper portions of the dermis 120 from unwanted damage while the pigmented cells 130 are being irradiated and/or damaged.

Figure 2A:
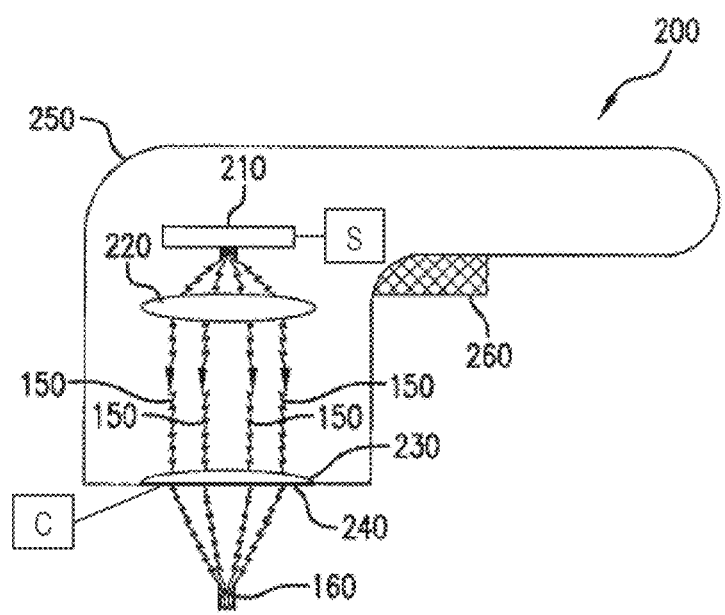
FIG. 2A is a cross-sectional side view of a diagram of another exemplary apparatus in accordance with exemplary embodiments of the present disclosure.

According to certain exemplary embodiments of the present disclosure, the window 240 can be provided as part of the second lens arrangement 230. For example, the second lens arrangement 230 can include a single plane-convex lens, as shown in FIG. 2A, or a plurality of plano-convex lenses, such as those shown in FIGS. 3A and 3D. Such lenses can be affixed to or formed as part of the window 240. The lower (planar) surface of such lenses can provide the benefits of the window 240 as described herein, e.g., precise positioning of the second lens arrangement 230 relative to the skin surface 100 to control depth of the focal regions 160 arrangements can be used in embodiments of the present disclosure.

The actuator arrangement 260 can be configured to activate and/or control the radiation emitter arrangement 210 and/or an external EMR source that provides radiation to the radiation emitter arrangement 210, such that the irradiation of an area of skin by the EMR 150 can be controlled. The radiation emitter arrangement 210 and/or the exemplary apparatus 200 can further include a conventional control arrangement (not shown) that can be configured to control and/or adjust the properties of the EMR 150 directed onto the skin being treated.

For example, the apparatus 200 can include one or more sensors S configured to detect contact of the apparatus 200 with the skin surface 100 and/or speed or displacement of the apparatus 200 over the skin surface 100 during use. Such exemplary sensors S can generate signals capable of varying properties of the EMR 150, e.g., by varying the power emitted by the radiation emitter arrangement 210 based on the translational speed of the apparatus 200, by turning off the source(s) of EMR 150 when the apparatus 150 is stationary relative to the skin surface 100, etc. Such sensors S and control arrangements can be provided as a safety feature, e.g. to prevent excessive irradiation and unwanted damage to the skin being treated, and are generally known in the art. Further variations of such conventional sensing and/or control arrangements can be used in embodiments of the present disclosure.

In general, it can be preferable to expose a particular location in the dermis to the focal region 160 for only a short period of time, e.g., to prevent local build-up of heat through absorption of the optical energy by melanin or other pigment. Long local irradiation times (or "dwell times") can generate heat faster and to a greater extent than it can safely diffuse into the surrounding tissue, which may lead to unwanted damage to unpigmented tissue. Thus, short-duration, intense irradiation of small areas of pigmented features 130 within the dermis 120 can disrupt the pigment and improve the appearance of melasma while avoiding excessive heat generation and unwanted thermal damage to surrounding unpigmented tissue. For example, typical sizes of pigmented cells or structures can be on the order of about 10 microns, and local thermal relaxation times can be on the order of about 0.1 to about 1-2 milliseconds. Longer local dwell times at irradiation intensities sufficient to heat and damage the pigmented structures 130 can build up heat locally faster than it can safely dissipate away.

Limiting irradiation times (dwell times) at a particular focal region location can be achieved in various ways. In one exemplary embodiment, the radiation emitter arrangement 210 can be configured to provide discrete pulses of EMR 150 into the focal regions 160. The interval between such pulses of EMR can be, e.g., on the order of about 50 milliseconds or more even if the location of the focal region is moving through the skin tissue at a relatively slow speed of a few mm/s. These exemplary parameters can result in a distance between focal regions 160 irradiated by successive pulses of, e.g., about 50-100 microns, which can be greater than a width of the focal region 160 itself. Accordingly, such general parameters can facilitate spatial and temporal separation of the successive irradiated focal regions 160, such that local thermal relaxation can occur and buildup of excess heat can be avoided. The spot size, pulse duration, and/or total pulse energy can be selected based on the principles and guidelines described herein, using simple calculations, to provide a sufficient fluence within the focal region 160 to affect the pigmented structures 130 while maintaining a sufficiently small dwell time (e.g. less than about 1-2 ms).

In further exemplary embodiments of the present disclosure, the focused radiation 150 can be scanned over a region of skin affected by dermal melasma, such that the focal region(s) 160 may irradiate and damage a large number of the pigmented cells 130. Such scanning can be performed with any of the embodiments described herein. The scanning can be done manually, e.g., using a conventional method of translating a handpiece over the area of skin to be treated.

Alternatively, the apparatus 200 can optionally be coupled to a translating arrangement that can be configured to automatically move the apparatus (or certain components thereof) over an area of skin to be treated. Such automatic translation can be provided as a pre-set pattern or as a random or semi-random path over the skin. In still further embodiments, one or more of the optical components (e.g. the first and/or second lens arrangement 220, 230) and/or the radiation emitter arrangement can be translated within the housing 250, such that the focal region(s) 160 can translate within the tissue while the housing 250 is held in a single position relative to the skin.

Average scan speeds (or ranges of such speeds) can be determined based on the general exemplary guidelines described herein. For example, for a particular spot size (which can be determined primarily by the properties of the optical arrangement), the local dwell (irradiation) time can be estimated as the spot size/width divided by the translational speed. As noted herein, such dwell time is preferably less than about 1-2 milliseconds to avoid local heat buildup and unwanted thermal damage of unpigmented tissue. Accordingly, a minimum scan speed can be estimated as the width of the focal region 160 divided by 1 millisecond. For example, a spot size of 10 microns (0.01 mm) would correspond to a minimum scan speed of 0.01 mm/0.001 seconds, or about 10 mm/sec (1 cm/sec). Scan rates for line-focused beams (e.g., produced by directing an EMR beam onto a cylindrical lens) can be estimated in a similar manner, e.g., where the width of the focal line corresponds to the width of the focal region and the scan speed is in a direction perpendicular to the focal line, or for other scanning configurations.

A power output of the radiation emitter arrangement 210 can be selected based on several factors including, e.g., the EMR wavelength, the number, size, and/or depth of the focal region(s) 160, optical characteristics and geometry of the first and second lens arrangements 220, 230, etc. The power output can be selected such that the fluence in the focal region 160 is sufficiently high to damage pigmented cells 130 that absorb the EMR 150 for short exposure times, while fluence at other depths (e.g., in the epidermis 110) is sufficiently low to minimize or avoid unwanted damage there.

Based on some experimental observations, a local fluence within the focal region 160 that may be sufficient to affect melanin-containing structures (e.g., pigmented cells) can be between about 10-1000 J/cm$^2$, for example, between about 50-500 J/cm$^2$, for EMR 150 having a wavelength of about 650 nm. This range of effective local fluences can increase slightly with increasing wavelength of the EMR 150 (and decrease with decreasing wavelength), based on the decreasing absorption factor for melanin at larger wavelengths. Larger or smaller local fluence values may also be provided when using faster or slower scan speeds, in further exemplary embodiments. Larger or smaller local fluence values can also be provided when using shorter or longer dwell times, respectively. The local dwell time can preferably remain less than about 1-2 milliseconds in such embodiments.

The exemplary fluence values and dwell times described herein can be understood to correspond to a single pulsed exposure onto, or a single traversal of a scanned focal region through, a particular location within the dermis. For example, a particular location within the dermis 120 may be irradiated by scanning more than one focal region 160 through it at different times, thereby providing a higher fluence at that location. However, local heat build-up can be avoided by providing a time interval between successive irradiations of the same location that is greater than a few milliseconds.

The total power output of the radiation emitter arrangement 210 directed onto a single focal spot 160 can thus be estimated and/or determined based on the focal spot size and scan speed. The fluence F (e.g., in J/cm$^2$) can be calculated as the EMR power output P multiplied by the dwell time z and divided by the focal spot area A (i.e., F=Pτ/A), where the dwell time τ can be estimated as the focal spot width D divided by the scan speed v (i.e., τ=D/v). As an exemplary calculation, for EMR 150 having a wavelength of about 650 nm, a focal spot width of about 20 microns, and a scan speed of about 1 cm/s, the power output P of a single EMR source (e.g., a laser diode) to achieve a level of local fluence in the focal region between about 10-1000 J/cm$^2$ is between about 15 mW and 1500 mW.

Typical scan speeds for a handpiece that is manually translated over an area of skin to be treated can be, e.g., on the order of about 5 mm/sec to about 5 cm/sec. Such speeds correspond to traversing a distance of 5 cm (about 2 inches) in about 1-10 seconds. Accordingly, for a handpiece that is translated manually over the skin to irradiate portions of the dermis as described herein, the power output and focal geometry of the apparatus 200 can be selected to provide a fluence at the irradiated locations within the dermis that is within the general range described herein.

Such exemplary power calculations can be based on the entire output of the laser diode being focused into one focal region. If the output from a single source of EMR is focused onto a plurality of focal regions (e.g., when using an optical splitter or a wide beam directed onto a plurality of micro-lenses), then the power output of the EMR source can be multiplied by the number of focal spots 160 to achieve the same local fluence within each focal region 160. EMR 150 can be provided as a continuous wave (CW) or optionally as a plurality of pulses. Alternatively, a plurality of EMR sources (e.g. laser diodes or the like) can be provided to generate a plurality of irradiated focal regions 160 simultaneously, with the appropriate power level for each EMR source being estimated as described above. In certain embodiments, if one or more EMR beams are scanned over the focusing lens arrangement 230, the power of the EMR source can be selected based on the lens properties, scan speed, etc. to provide fluences and dwell times at locations of the dermis irradiated by the focal regions 160 that are within the general ranges described herein.

In certain exemplary embodiments of the present disclosure, the radiation emitter arrangement 210 can include a plurality of EMR emitters (e.g., laser diodes or waveguide ends). Such emitters can be provided in a linear array, such that they lie substantially along one or more straight lines. In further exemplary embodiments, the emitters can be arranged in a two-dimensional pattern, which can provide further patterns of EMR 150 directed onto the first lens arrangement 220. As described above, the power output of each emitter can be selected using a routine calculation based on the focal spot size and scan speed to generate a local fluence within each focal zone 160 that is within the preferred range described herein.

Figure 4:
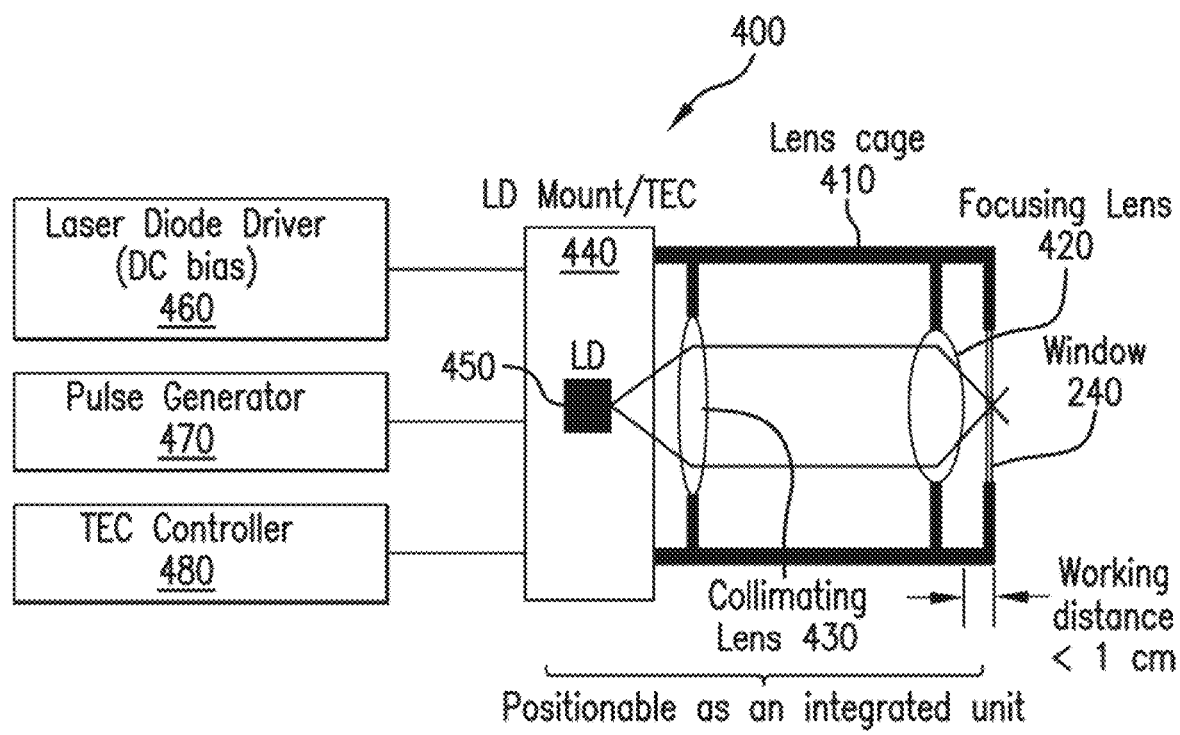
FIG. 4 is a schematic cross-sectional side view of a further exemplary apparatus in accordance with still further exemplary embodiments of the present disclosure.

A schematic diagram of a further exemplary apparatus 400 in accordance with certain exemplary embodiments of the present disclosure is shown in FIG. 4. The exemplary apparatus 400 can be generally similar to the apparatus 200 shown in FIG. 2, and illustrates a few further features which may also be provided in the apparatus 200 such as, e.g., a cooling arrangement for the EMR source or a lens cage.

Exemplary features of the exemplary apparatus 200 can also be used with the exemplary apparatus 400, including but not limited to an array of micro-lenses 300, a housing 250, etc.

The apparatus 400 includes a lens cage 410 that can be provided as an enclosure or housing that encloses optical lenses 420, 430. A window 240 can be provided at one end of the lens cage 410. An aspheric focusing lens 420 can be used in certain embodiments to provide a larger front surface working distance than, e.g., a microscope objective lens. The distance between the front of the focusing lens 420 and the target tissue may be less than about 1 cm for large NA values as described herein, such that the window 240 can also protect the lens 4 from contacting the tissue directly. The NA of the aspheric focusing lens 420 can optionally be selectable, e.g. to vary the focal depth beyond the window 240.

The exemplary apparatus 400 further includes a laser diode (LD) mounting arrangement 440 coupled to the lens cage 410, which can accept one or more laser diodes 450 that can be selected to emit energy in the visible and/or NIR ranges. A driver 460 for the laser diode(s) 450 can be provided, and the laser diodes 450 can be held slightly above threshold during operation with an applied DC bias current, which can facilitate a rapid rise-time in the pulse activation of the diode(s) 450. The pulse properties can be controlled by a pulse generator arrangement 470, e.g. a programmable function generator that can be configured to control the laser diode(s) 450 to produce single pulses or sequences of pulses, with selectable pulse widths (e.g. 30 ns and greater) and intervals between pulses.

The LD mounting arrangement 440 can also include a thermoelectric cooler (TEC) arrangement coupled or connected to the laser diode mounting arrangement 440, which can be controlled (e.g. with a TEC controller 480) to prevent the laser diode(s) 450 from overheating during use. The apparatus 400 (as well as the apparatus 200 shown in FIG. 2) can be used in various orientations, e.g., vertically, horizontally, etc., with the window 240 pressed against a tissue provided at any angle to precisely position the optics relative to the tissue surface and thereby facilitate control of the focal depth of the beam within the tissue.

The exemplary apparatus 200 shown in FIG. 2 and the exemplary apparatus 400 shown in FIG. 4 are illustrations of exemplary configurations, and other embodiments using various combinations and/or configurations of similar components can also be used. For example, different numbers and/or types of optical arrangements 220, 230 and/or emitter arrangements 210 can be used to provide irradiation characteristics and focal regions 160 within the dermis 120 as described herein. For example, in certain embodiments, the apparatus 200 can be provided in a shape factor similar to that of a handheld razor, with the radiation emitter arrangement 210 provided as one or more laser diodes, optical arrangements 220, 230 provided in the "head" of the razor, and a power source (e.g. one or more conventional alkaline cells or the like) provided in the handle. Other form factors can also be used in further embodiments of the disclosure. Similar features, combinations and/or variations can be provided for the apparatus 400.

Exemplary properties of the radiation emitter arrangement 210, such as, e.g., wavelength(s) of EMR 150, power or intensity of the EMR 150, size and numerical apertures of the optical arrangements 220, 230, scanning speed or rate of the first optical arrangements 220 (if present), and/or target scan speed (or range thereof) of the apparatus 200 over the area of skin being treated, can be selected to provide appropriate fluence, intensity and/or dwell time of the EMR 150 on the pigmented cells during operation of the apparatus 200. Exemplary values and/or ranges for such parameters, as well as certain basic approaches that can be used to estimate their values as needed, are described in more detail herein. For example, such exemplary parameters can be selected to provide sufficient local fluence at the pigmented cells 130 to damage them and reduce the pigmented appearance of the skin, while avoiding unwanted damage to the epidermis 110 and unpigmented volumes of the dermis 120.

The exemplary effective dwell time can be estimated using conventional techniques based on an approximate width of pigmented cells 130 of about 10 µm and the local width (e.g., focal diameter or width) and speed of the focal region 160. The speed of the focal region 160 can be estimated based on a scan speed of EMR 150 provided by the first lens arrangement 220 and/or radiation emitter arrangement 210 (if present), optical geometry of the optical arrangements 220, 230, and scan speed of the apparatus 200 over the area of skin being treated.

One or more exemplary parameters of the apparatus 200, 400 can be selected and/or adjusted once the other ones are known to provide a safe but effective irradiation of the pigmented cells 130 as described herein. For example, the exemplary apparatus 200, 400 having known geometry (e.g. spot size or focal line width, and NA) of the lens arrangements 220, 230 or lenses 420, 430 (and internal scanning speed of EMR beams, if present), and a particular wavelength of EMR 150 can be provided. The power of the EMR source(s) can then be selected based on a target range of scanning speeds of the apparatus 200 over the area to be treated. For example, the exemplary apparatus 200, 400 can be traversed over an area of skin at a speed between about 1-5 cm/s, which corresponds approximately to the speed at which a conventional razor is traversed over skin during shaving. Using these exemplary parameters and the number of passes to be made over the treatment area, the local speed and dwell time of the focal region(s) 160 can be estimated, and a power output of the radiation emitter arrangement 210 can be selected or adjusted to provide an effective local fluence within the focal region 160 as described herein. Such calculations are routine and can be done by a person of ordinary skill in the art.

In further exemplary embodiments of the present disclosure, a method for reducing the pigmented appearance of dermal melasma can be provided. The exemplary method can include directing and focusing electromagnetic radiation 150 as described herein onto a plurality of focal regions 160 within the dermis 120 using an optical arrangement, such that the EMR 150 is selectively absorbed by pigmented regions 130 to thermally damage or disrupt them, while avoiding unwanted thermal damage to unpigmented regions and overlying tissue (e.g., the epidermis 110).

The EMR 150 can have a wavelength greater than about 600 nm, e.g., between about 600 and 850 nm, or between 625 and 800 nm, or between about 650 and 750 nm. A width of the focal region within the dermis can be less than about 200 microns, e.g., less than about 100 microns, or less than about 50 microns. The spot size can be greater than the theoretical lower limit of a few microns.

The EMR 150 can be focused using the optical arrangement, which can include one or more lens arrangements 220, 230. The focusing lens arrangement 230 having a high NA, e.g., between about 0.5 and 0.9, can be used to focus the EMR 150 onto a focal region 160. Such NA values can facilitate generation of high fluence in the focal regions 160 within the dermis 120 while avoiding large fluences that may generate unwanted damage in the overlying tissue. Such focusing can be achieved using, e.g., the single focusing lens 230 (such as a convex objective lens or a plano-convex lens), a plurality of such lenses provided as an array of micro-lenses 300, one or more convex or plano-convex cylindrical lenses, or the like. The EMR 150 can be directed onto the focusing lens arrangements 230, and optionally scanned or pulsed over the one or more focusing lens arrangements 230, to irradiate a plurality of focal regions 160 in the dermis 120, either simultaneously or sequentially.

In further exemplary embodiments of the present disclosure, an optical gel or the like (e.g. glycerol or a similar substance) can be provided between the window 240 and the skin surface 100 as a topical application to the skin surface 100. Such a gel can reduce an optical index mismatch between the window 240 and the skin, and it may improve transmission of the EMR 150 from the apparatus 200 into the dermis 120. The gel can also reduce friction between the exemplary apparatus 200 and skin surface 100, thereby facilitating a smoother translation of the apparatus 200 over the area of skin being treated.

A particular location within the dermis 120 can be irradiated by the focal region with an irradiation (dwell) time that is less than about 2 milliseconds, e.g., to facilitate local thermal relaxation of tissue that absorbs the EMR 150 and avoid local buildup of excess heat. Such short dwell times can be provided, e.g., by scanning an apparatus that provides the focused EMR 150 over the area of skin being treated, by pulsing the EMR source, and/or by moving components of the EMR source or emitter 210 and/or optical arrangement, such that the location of the focal region(s) 160 within the dermis 120 varies with time.

The local fluence within the focal region 160 can be, e.g., between about 10-1000 J/cm$^2$, e.g., between about 50-500 J/cm$^2$, for EMR 150 having a wavelength of about 650 nm. This range of effective local fluences can increase slightly with increasing wavelength of the EMR 150 (and decrease with decreasing wavelength), based on the decreasing absorption factor for melanin at larger wavelengths. Such fluence can be related to the focal properties of the optical arrangement (e.g., the focal spot size), the translational speed of the focal region 160 within the dermis 120, pulse duration of the applied EMR 150, etc. The surface of the skin 100 can optionally be cooled to further prevent unwanted thermal damage in the epidermis and/or upper dermis.

The exemplary method and apparatus and the associated parameters described herein can be generally based on a single pass of a focal region 160 over a pigmented cell 130. The fluence needed to achieve the same thermal damage effect based on a plurality of passes varies approximately as the fourth root of the number of passes n. For example, a single pass of a focal region 160 over a pigmented cell 130 at a particular fluence would have a similar effect as 16 passes made with a focal region 160 having half the particular fluence. Although a single pass may be more efficient than a plurality of passes, the exemplary apparatus 200, 400 can be configured to provide an effective fluence after a particular number of passes have been made. A plurality of passes can provide a greater safety margin to avoid unwanted damage to the epidermis while damaging the pigmented cells 130, e.g., it can accommodate a greater range of effective translation speeds of the apparatus 200 over the treated area for multiple passes as compared to if just a single pass is made. The number of passes of the focal region(s) 160 through a particular location in the dermis 120 can depend, e.g., on the internal scan rate of EMR 150 over the second lens arrangement 230, if present, the number of focal regions 160 that may pass through a given location during one pass of the entire apparatus 200 (e.g., a function of the number, size, and arrangement of micro-lenses 300, if present), as well as the number of times the apparatus 200 is translated over the area to be treated.

Other exemplary features and/or functions of the exemplary apparatus 200, 400 described herein can also be used in conjunction with the exemplary disclosed methods for treating dermal melasma.

Example

An animal study using an exemplary spot-focused laser device and model system were used to test the efficacy of treating deep melasma using optical radiation. The study was performed on a female Yorkshire pig, as described below.

First, a deep-melasma condition was simulated by tattooing the dermis using a melanin-based ink. The ink was prepared by mixing synthetic melanin at a concentration of 20 mg/mL in a 50:50 saline/glycerol solution. The resulting suspension was then agitated prior to being injected into 1 cm by 1 cm test sites on the animal subject using a standard tattoo gun. The tattooed sites were then allowed to settle over a period of a week to allow melanophages to phagocytoze the melanin granules in the dermis. The melanin left in the epidermis was substantially eliminated over this time period through natural bodily processes.

Figure 5:
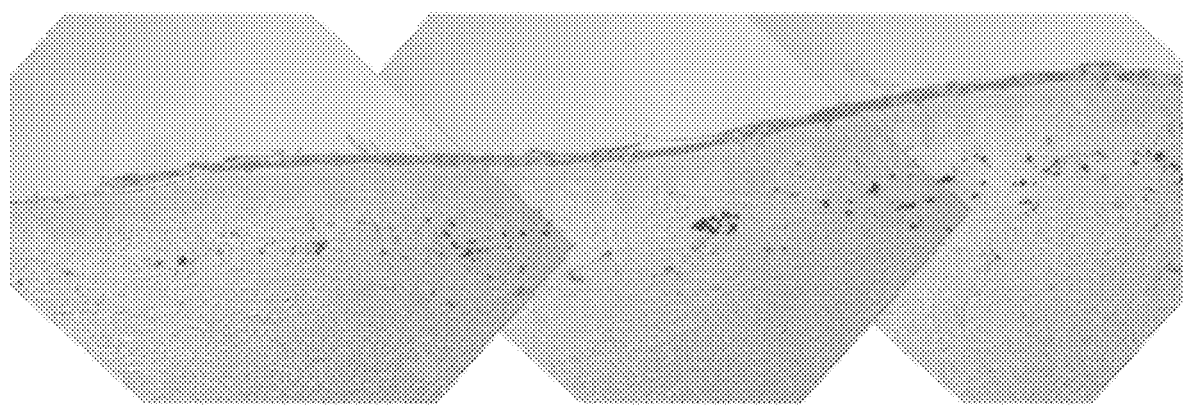
FIG. 5 is an exemplary biopsy image of pig skin tattooed with a melanin solution to simulate the effects of dermal melasma.

An exemplary biopsy image from a tattooed site that was allowed to settle as described herein, is shown in FIG. 5. The tissue sample was stained with Fontana-Masson stain to better image any melanin present. The dark spots evident in the dermal layer in FIG. 5 appear to be generally similar to those observed in patients having deep/dermal melasma. No such dark spots were seen in biopsy samples taken from untattooed sites that were similarly stained. Accordingly, the tattoo process described herein appears to provide a useful in vivo model of dermal melasma.

An exemplary melasma treatment system was constructed based on exemplary embodiments of the present disclosure described herein, which includes a 200 mW continuous wave (CW) diode laser configured to emit optical energy having a wavelength of about 658 nm, mounted on an x-y scanning platform. The scanner was capable of scanning speeds up to 15 mm/s. The laser beam was collimated and focused using two lenses having a numerical aperture (NA) of 0.62 to a depth of about 200 μm.

Test sites that were tattooed with melanin ink as described above, and control sites that have only tattooed borders to outline them, were both treated by scanning the focused laser beam across the sites in 10 parallel lines at different speeds. The control sites were scanned to assess any potential damage that may occur in unpigmented skin under the different scanning conditions performed.

Figure 6A:
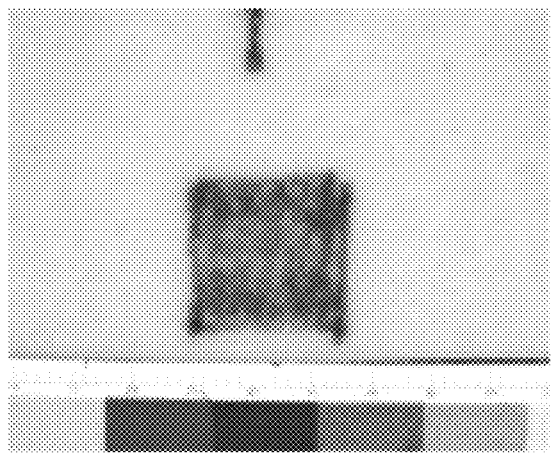
FIG. 6A is an exemplary surface image of a region of pig skin tattooed with a melanin solution to simulate the effects of dermal melasma.
Figure 6B:
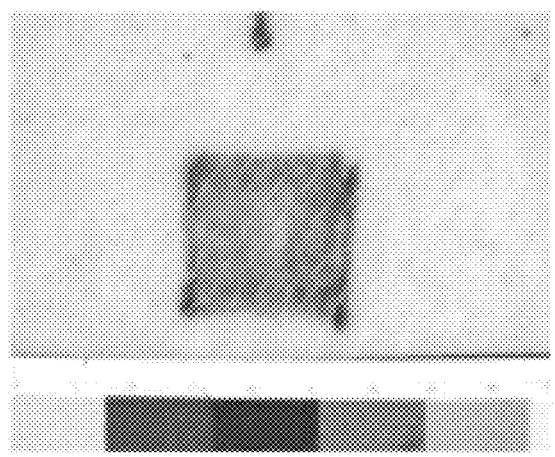
FIG. 6B is an exemplary surface image of the tattooed region of pig skin shown in FIG. 6A after it has been irradiated with focused electromagnetic radiation in accordance with exemplary embodiments of the present disclosure.

An exemplary tattooed test site is shown in FIG. 6A. This image shows the test site after the tattoo has been allowed to settle for a week, just prior to scanning with the laser apparatus. The test site was scanned with the laser at a speed of 1-3 mm/sec, using a 200 mW CW output. The same test site is shown in FIG. 6B two weeks after it was scanned with the laser. There is a noticeable lightening of the appearance with no scarring or scabbing evident, even though only a portion of the tattooed area was irradiated with focused optical energy. These results indicate the general efficacy of the exemplary methods and devices described herein for reducing the hyperpigmented appearance of deep/dermal melasma.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure. All patents and publications cited herein are incorporated herein by reference in their entireties.

What is claimed is:

1. A method, comprising:
    generating, by a radiation arrangement, at least one electromagnetic radiation (EMR) beam having a wavelength between 600 nm and 850 nm;
    focusing, by an optical arrangement including at least one lens, the at least one EMR beam into a plurality of focal regions within a dermis layer of skin tissue containing pigmented and unpigmented regions, wherein a width of at least one of the plurality of focal regions is less than 100 μm; and
    scanning the plurality of focal regions of the at least one EMR beam over an entirety of a treatment area of the skin tissue within the dermis layer, wherein a dwell time of the least one EMR beam at the plurality of focal regions is 2 ms or less;
    controlling, using a controller,
        a power output of the radiation arrangement to provide a fluence of the at least one EMR beam within each focal region of the plurality of focal regions of between 10 to 1000 J/cm$^2$, and
        at least one of the radiation arrangement or the optical arrangement to scan the at least one EMR beam at a scan speed of 5 mm/s to 5 cm/sec,
    wherein the at least one EMR beam provides selective energy absorption by the pigmented regions of the skin tissue within the treatment area and damages of the pigmented region while preventing damage to the unpigmented regions of the skin tissue within the plurality of focal regions and an epidermal layer of the skin tissue overlying the plurality of focal regions.

2. The method of claim 1, wherein the optical arrangement comprises a plurality of microlenses.

3. The method of claim 2, further comprising directing a single EMR beam over at least a portion of the array of micro-lenses to produce the plurality of focal regions simultaneously.

4. The method of claim 2, further comprising directing a single EMR beam over at least a portion of the array of micro-lenses to produce the plurality of focal regions non-sequentially.

5. The method of claim 2, wherein the micro-lens array is a square or rectangular array.

6. The method of claim 2, wherein the micro-lens array is a hexagonal array.

7. The method of claim 2, wherein a width of the micro-lenses is between 1 mm and 3 mm.

8. The method of claim 2, wherein the plurality of micro-lenses are cylindrical lenses.

9. The method of claim 8, further comprising traversing the EMR beam in a direction that is lateral to a longitudinal axis of the cylindrical micro-lenses.

10. The method of claim 2, further comprising placing the array of micro-lenses in contact with the skin tissue during generation of the at least one EMR beam.

11. The method of claim 1, further comprising generating a plurality of EMR beams by a plurality EMR sources to produce the plurality of focal regions simultaneously.

12. The method of claim 1, wherein a numerical aperture of the at least one lens is between 0.5 and 0.9.

13. The method of claim 1, wherein the plurality of focal regions are located at different depths below a surface of the skin tissue.

14. The method of claim 13, wherein the depth of the plurality of focal regions is between 120 microns and 400 microns below the surface of the skin tissue.

15. The method of claim 1, wherein the fluence is between 50 to 500 J/cm$^2$.

16. The method of claim 1, further comprising cooling, using a cooling arrangement, the surface of the skin tissue.

17. The method of claim 1, wherein the dwell time is 1 ms or less.

18. The method of claim 1, further comprising applying a gel to the surface of the skin tissue prior to contacting the at least one portion of the apparatus to the surface of the skin tissue.

19. The method of claim 1, wherein the radiation arrangement comprises at least one laser diode.

20. The method of claim 1, wherein the radiation arrangement comprises at least one of a waveguide or an optical fiber.

21. A method, comprising:
  generating, by a radiation arrangement, at least one electromagnetic radiation (EMR) beam having a wavelength between 600 nm and 850 nm;
  focusing, by an optical arrangement including at least one lens having a numerical aperture between 0.5 and 0.9, the at least one EMR beam into a plurality of focal regions within a dermis layer of skin tissue containing pigmented and unpigmented regions, wherein the at least one EMR beam provides selective energy absorption by the pigmented regions of the skin tissue within the treatment area, and wherein a width of at least one of the plurality of focal regions is less than 100 μm;
  scanning the plurality of focal regions of the at least one EMR beam over a treatment area of the skin tissue within the dermis, wherein a dwell time of the least one EMR beam at the plurality of focal regions is 2 ms or less; and
  controlling, using a controller,
    the radiation arrangement to emit the at least one EMR beam at a power output between 0.004 to 79 W, and
    at least one of the radiation arrangement or the optical arrangement to scan the at least one EMR beam at a scan speed of 5 mm/s to 5 cm/sec;
  wherein the at least one EMR beam damages the pigmented regions of the skin tissue within the plurality of focal regions while preventing damage to the unpigmented regions of the skin tissue within the plurality of focal regions and an epidermal layer of the skin tissue overlying the plurality of focal regions.

* * * * *